United States Patent
Goto et al.

(10) Patent No.: US 12,169,932 B2
(45) Date of Patent: Dec. 17, 2024

(54) INFORMATION PROCESSING DEVICE, PROGRAM, TRAINED MODEL, DIAGNOSTIC SUPPORT DEVICE, LEARNING DEVICE, AND PREDICTION MODEL GENERATION METHOD

(71) Applicant: FUJIFILM Corporation, Tokyo (JP)

(72) Inventors: Tsubasa Goto, Tokyo (JP); Caihua Wang, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 380 days.

(21) Appl. No.: 17/565,412

(22) Filed: Dec. 29, 2021

(65) Prior Publication Data
US 2022/0122253 A1 Apr. 21, 2022

Related U.S. Application Data

(63) Continuation of application No. PCT/JP2020/028074, filed on Jul. 20, 2020.

(30) Foreign Application Priority Data

Jul. 26, 2019 (JP) .................................. 2019-137875
Mar. 4, 2020 (JP) .................................. 2020-036935

(51) Int. Cl.
*G06T 7/00* (2017.01)
*G06V 10/80* (2022.01)
(Continued)

(52) U.S. Cl.
CPC .......... *G06T 7/0012* (2013.01); *G06V 10/811* (2022.01); *G06V 10/82* (2022.01);
(Continued)

(58) Field of Classification Search
CPC ......... G06T 7/0012; G06T 2207/10088; G06T 2207/20081; G06T 2207/20084;
(Continued)

(56) References Cited

U.S. PATENT DOCUMENTS

2011/0046451 A1* 2/2011 Horn ..................... G06T 7/0012
382/128
2015/0254554 A1 9/2015 Kato
(Continued)

FOREIGN PATENT DOCUMENTS

JP 2008157640 7/2008
JP 2011521220 7/2011
(Continued)

OTHER PUBLICATIONS

Spasov Simeon et al: "A parameter-efficient deep learning approach to predict conversion from mild cognitive impairment to Alzheimer's disease", Neuroimage, vol. 189, Jan. 14, 2019 (Jan. 14, 2019), pp. 276-287, P085636020, ISSN: 1053-8119, DOI:10.1016/J. Neuroimage. Jan. 31, 2019 (Year: 2019).*
(Continued)

*Primary Examiner* — John J Lee
(74) *Attorney, Agent, or Firm* — JCIPRNET

(57) ABSTRACT

Provided are an information processing device, a program, a trained model, a diagnostic support device, a learning device, and a prediction model generation method that can perform prediction with high accuracy using images. An information processing device includes: an information acquisition unit that receives an input of image data and non-image data related to a target matter; and a prediction unit that predicts an aspect related to the matter at a time different from a time when the image data is captured on the basis of the image data and the non-image data input through the information acquisition unit. The prediction unit performs weighting calculation by a calculation method, which outputs a combination of products of elements of a first feature amount calculated from the image data and a second feature amount calculated from the non-image data, to calculate a third feature amount in which the first feature
(Continued)

amount and the second feature amount are fused and performs the prediction on the basis of the third feature amount.

20 Claims, 13 Drawing Sheets

(51) Int. Cl.
*G06V 10/82* (2022.01)
*G16H 30/40* (2018.01)
*G16H 50/20* (2018.01)

(52) U.S. Cl.
CPC ............ *G16H 30/40* (2018.01); *G16H 50/20* (2018.01); *G06T 2207/10088* (2013.01); *G06T 2207/20081* (2013.01); *G06T 2207/20084* (2013.01); *G06T 2207/20221* (2013.01); *G06T 2207/30016* (2013.01)

(58) Field of Classification Search
CPC ........... G06T 2207/20221; G06T 2207/30016; G16H 50/20; G16H 30/40; G06V 10/82; G06V 10/811
See application file for complete search history.

(56) References Cited

U.S. PATENT DOCUMENTS

| | | | |
|---|---|---|---|
| 2019/0005399 | A1 | 1/2019 | Noguchi et al. |
| 2019/0019080 | A1* | 1/2019 | Claessens ............... G06N 3/047 |
| 2022/0253699 | A1* | 8/2022 | Hoshen .................... G06N 3/08 |
| 2022/0366660 | A1* | 11/2022 | Raschke ................ B25J 9/1697 |

FOREIGN PATENT DOCUMENTS

| | | |
|---|---|---|
| JP | 2015166962 | 9/2015 |
| JP | 2019008742 | 1/2019 |
| JP | 6483890 | 3/2019 |
| WO | 2019086555 | 5/2019 |

OTHER PUBLICATIONS

Saman Sarraf et al., "DeepAD: Alzheimer's Disease Classification via Deep Convolutional Neural Networks using MRI and fMRI," bioRxiv, Aug. 2016, pp. 1-32.

Garam Lee et al., "Predicting Alzheimer's disease progression using multi-modal deep learning approach," Scientific Reports, Feb. 2019, pp. 1-12.

Simeon Spasov et al., "A parameter-efficient deep learning approach to predict conversion from mild cognitive impairment to Alzheimer's disease," NeuroImage, vol. 189, Apr. 2019, pp. 276-287.

Siemon E. Spasov et al., "A Multi-modal Convolutional Neural Network Framework for the Prediction of Alzheimer's Disease," 2018 40th Annual International Conference of the IEEE Engineering in Medicine and Biology Society, Jul. 2018, pp. 1271-1274.

"International Search Report (Form PCT/ISA/210) of PCT/JP2020/028074," mailed on Sep. 15, 2020, with English translation thereof, pp. 1-7.

"Written Opinion of the International Searching Authority (Form PCT/ISA/237)" of PCT/JP2020/028074, mailed on Sep. 15, 2020, with English translation thereof, pp. 1-6.

Yinghao Chu et al., "Short-term reforecasting of power output from a 48 MWe solar PV plant", Solar Energy, Dec. 11, 2014, pp. 68-77.

Hongming Li et al., "Early Prediction of Alzheimer's Disease Dementia Based on Baseline Hippocampal MRI and 1-YEAR Follow-Up Cognitive Measures Using Deep Recurrent Neural Networks", 2019 IEEE 16th International Symposium on Biomedical Imaging, Apr. 8, 2019, pp. 368-371.

"Search Report of Europe Counterpart Application", issued on Aug. 24, 2022, p. 1-p. 10.

"Office Action of Europe Counterpart Application", issued on Oct. 2, 2023, with English translation thereof, p. 1-p. 8.

Heung-Il Suk et al., "Hierarchical feature representation and multimodal fusion with deep learning for AD/MCI diagnosis," NeuroImage, vol. 101, Jul. 2014, pp. 569-582.

Manhua Liu et al., "Multi-Modality Cascaded Convolutional Neural Networks for Alzheimer's Disease Diagnosis," Neuroinformatics, vol. 16, Mar. 2018, pp. 295-308.

* cited by examiner

Bi-linear $$z_k = \sum_{ij} w_{ijk} x_i y_j$$

Bi-linear shake $$z_k = \sum_{ij} w_{ijk}\{\alpha(x_i - 1) + 1\}\{(\alpha - 1)(y_j - 1) + 1\}$$

INFORMATION PROCESSING DEVICE, PROGRAM, TRAINED MODEL, DIAGNOSTIC SUPPORT DEVICE, LEARNING DEVICE, AND PREDICTION MODEL GENERATION METHOD

CROSS-REFERENCE TO RELATED APPLICATIONS

The present application is a Continuation of PCT International Application No. PCT/JP2020/028074 filed on Jul. 20, 2020 claiming priorities under 35 U.S.C. § 119(a) to Japanese Patent Application No. 2019-137875 filed on Jul. 26, 2019 and Japanese Patent Application No. 2020-036935 filed on Mar. 4, 2020. Each of the above applications is hereby expressly incorporated by reference, in its entirety, into the present application.

BACKGROUND OF THE INVENTION

1. Field of the Invention

The present invention relates to an information processing device, a program, a trained model, a diagnostic support device, a learning device, and a prediction model generation method, and more particularly, to an artificial intelligence technique that predicts an unknown matter using an image.

2. Description of the Related Art

In recent years, advances in medical apparatuses, such as a computed tomography (CT) apparatus and a magnetic resonance imaging (MRI) apparatus, have made it possible to perform image diagnosis using high-resolution medical images with higher quality. In particular, since a lesion region can be accurately specified by image diagnosis using CT images, MRI images, and the like, an appropriate treatment is performed on the basis of the specification result. In addition, there is a technique which analyzes a medical image with computer-aided diagnosis (CAD) using a discriminator trained by deep learning and the like, extracts the region, position, volume, and the like of a lesion included in the medical image, and acquires the extracted results as analysis results.

On the other hand, in recent years, with the advent of an aging society, the number of patients with dementia diseases has increased year by year. Dementia develops in a case in which the atrophy of the brain progresses due to the accumulation of a protein called amyloid beta in the brain and cognitive ability is reduced. Treatments for dementia are being studied, but there is still no cure for dementia. Therefore, it is important to detect the atrophy of the brain in its early stages and to start a treatment to slow down the progression of dementia in its early stages in order to maintain the quality of life.

In recent years, information related to the state of the brain can be acquired by nuclear medicine examinations, such as single photon emission computed tomography (SPECT) and positron emission tomography (PET), CT images acquired by a CT apparatus, and MRI images acquired by an MRI apparatus in order to meet the demands. For example, a reduction in the blood flow and metabolism of a local part of the brain can be detected by seeking a change in the local part of the brain over time using SPECT and PET images. Further, in recent years, the relationship between the degree of atrophy of the brain and the degree of progression of dementia has been studied. The atrophy of the brain can be detected by calculating the volume of a specific part of the brain using MRI images and comparing a change in the volume over time. For example, SARRAF, Saman, et al. "DeepAD: Alzheimer's Disease Classification via Deep Convolutional Neural Networks using MRI and fMRI." bioRxiv, 2016, 070441 proposes a method which automatically discriminates a normal brain image and a dementia brain image using machine learning.

JP6483890B discloses a diagnostic support device that analyzes a brain image to predict whether or not a patient with mild cognitive impairment will develop Alzheimer's disease within a predetermined period. SARRAF, Saman, et al. "DeepAD: Alzheimer's Disease Classification via Deep Convolutional Neural Networks using MRI and fMRI." bioRxiv, 2016, 070441 proposes a method for predicting whether or not mild cognitive impairment (MCI) will progress to Alzheimer's disease using a multi-modal recurrent neural network.

SUMMARY OF THE INVENTION

For various diseases including dementia, it is desirable to predict the progression of the diseases to support diagnosis by the doctor, in order to select the best treatment method at the present time, such as a treatment method for delaying the progression of the diseases. For example, it is desirable to determine whether a patient with MCI will progress to Alzheimer's disease in the future.

SARRAF, Saman, et al. "DeepAD: Alzheimer's Disease Classification via Deep Convolutional Neural Networks using MRI and fMRI." bioRxiv, 2016, 070441 discloses a technique for determining whether a patent has Alzheimer's disease or is in a normal state from the MRI image of the brain, but does not disclose the content of predicting the future. JP6483890B and Garam Lee, Kwangsik Nho, et al. "Predicting Alzheimer's disease progression using multi-modal deep learning approach", Scientific Reports 9, Article number: 1952 (2019) disclose a technique for determining whether or not a patient will progress to Alzheimer's disease in the future, but the accuracy of the determination is not sufficient.

This problem is not limited to the prediction of the future progression of a disease based on medical images, but is understood as a problem common to the process of predicting the future aspect or the past aspect of various matters related to a temporal change. It is also required to improve the accuracy of prediction in, for example, a social infrastructure inspection to predict the future deterioration state of structures from the images of the structures, such as bridges or buildings, or verification to predict an aspect at a certain point of time in the past from the image showing the current state.

The invention has been made in view of the above-mentioned circumstances, and an object of the invention is to provide an information processing device, a program, a trained model, a diagnostic support device, a learning device, and a prediction model generation method that can perform prediction with high accuracy using images.

According to an aspect of the present disclosure, there is provided an information processing device comprising: an information acquisition unit that receives an input of image data and non-image data related to a target matter; and a prediction unit that predicts an aspect related to the matter at a time different from a time when the image data is captured on the basis of the image data and the non-image data input through the information acquisition unit. The prediction unit performs weighting calculation by a calculation method, which outputs a combination of products of elements of a first feature amount calculated from the image data and a second feature amount calculated from the non-image data, to calculate a third feature amount in which the first feature amount and the second feature amount are fused and performs the prediction on the basis of the third feature amount.

According to this aspect, in a case in which the aspect at a time different from the time when the image data is captured is predicted on the basis of the combination of the image data and the non-image data, the prediction is performed using the third feature amount including elements of the product of the first feature amount obtained from the image data and the second feature amount obtained from the non-image data. Therefore, the accuracy of prediction can be higher than that in a case in which a simple linear connection (linear method) is adopted.

The term "prediction" includes the concept of inference, estimation, and determination and includes the concept of both a case in which an aspect at a time after the time when the image data is captured is predicted and a case in which an aspect at the past time before the time when the image data is captured is predicted.

The "time when the image data is captured" refers to the time when the imaging of an object for acquiring image data is performed. Since the image data is the content of the image indicating the state of the object at the time of imaging, the "time when the image data is captured" may be understood as the time when the state of the content of the image indicated by the image data is understood. The term "time" is not limited to a case in which a specific point of "time" is exactly indicated, but may include a time range that is evaluated to be approximately the same time from the point of view of a common-sense measure of the speed of a change in the target matter over time. In addition, even in a case in which it is difficult to clearly specify the time when the image data is captured, it is possible to perform a prediction process, regarding at least the time when the image data is input to the information processing device as the "time when the image data is captured".

The "time different from the time when the image data is captured" is a comprehensive expression including the concept of both a case of designating a time after the time when the image data is captured and a case of designating a time before the time when the image data is captured.

In the information processing device according to another aspect of the present disclosure, the prediction unit may include a trained prediction model that has been subjected to machine learning so as to receive the input of the image data and the non-image data and to output, as a result of the prediction, information indicating the aspect related to the matter at a time different from the time when the image data is captured.

In the information processing device according to still another aspect of the present disclosure, the prediction unit may be configured using a neural network.

In the information processing device according to yet another aspect of the present disclosure, the prediction unit may perform a class classification process of determining which of a plurality of classes corresponding to each of a plurality of candidates for the aspect related to the matter at a time different from the time when the image data is captured the aspect belongs to in response to the input of the image data and the non-image data and may output a result of the class classification process.

In the information processing device according to still yet another aspect of the present disclosure, the prediction unit may perform a two-class classification process of determining whether an aspect after a lapse of a specific period from the time when the image data is captured or a past aspect before a specific period from the time when the image data is captured as the aspect related to the matter at a time different from the time when the image data is captured is a first state or a second state different from the first state and may output a result of the two-class classification process.

In the information processing device according to yet still another aspect of the present disclosure, the prediction unit may include: a first processing unit that calculates the first feature amount from the image data; a second processing unit that calculates the second feature amount from the non-image data; and a third processing unit that performs the weighting calculation by the calculation method that outputs the combination of the products of the elements of the first feature amount and the second feature amount to calculate the third feature amount.

In the information processing device according to still yet another aspect of the present disclosure, the weighting calculation performed by the third processing unit may include a process of multiplying the first feature amount and the second feature amount at a random ratio.

In the information processing device according to yet still another aspect of the present disclosure, the first processing unit may be configured using a first neural network including a plurality of convolutional layers and a first fully connected layer, and the second processing unit may be configured using a second neural network including a second fully connected layer.

The information processing device according to still yet another aspect of the present disclosure may further comprise a third fully connected layer that calculates a final output value from the third feature amount.

In the information processing device according to yet still another aspect of the present disclosure, the non-image data may include data of information related to a matter that does not appear in an image indicated by the image data.

In the information processing device according to still yet another aspect of the present disclosure, the non-image data may include data of information including information at a plurality of points of time.

In the information processing device according to yet still another aspect of the present disclosure, the target matter may be a health condition of a subject, the image data may be a medical image obtained by imaging the subject, the non-image data may include biological information of the subject, and the prediction unit may predict the health condition of the subject after a lapse of a specific period from a time when the medical image is captured or the health condition of the subject at a past time before a specific period from the time when the medical image is captured.

The term "health condition of the subject" includes various concepts of conditions related to the health of the subject, such as the disease state of the subject, the progression of a disease, or whether or not the subject is a healthy person.

In the information processing device according to still yet another aspect of the present disclosure, the target matter may be a disease state of a subject with mild cognitive impairment, the image data may be a magnetic resonance Imaging (MRI) image obtained by imaging a brain of the subject, the non-image data may include at least one of blood test data, genetic data, or a cognitive ability score of the subject, and age and gender of the subject, and the prediction unit may predict whether the disease state of the subject will be Alzheimer's disease or the mild cognitive impairment after a lapse of a specific period from a time when the MRI image is captured.

In the information processing device according to yet still another aspect of the present disclosure, the prediction unit may exclude the subject, from which a prediction result indicating that the disease state of the subject will be the mild cognitive impairment after the lapse of the specific period, from subjects of a clinical trial.

According to still yet another aspect of the present disclosure, there is provided an information processing device comprising: a processor; and a non-transitory computer-readable medium on which a program executed by the processor is recorded. According to commands of the program, the processor receives an input of image data and non-image data related to a target matter, performs weighting calculation by a calculation method, which outputs a combination of products of elements of a first feature amount calculated from the image data and a second feature amount calculated from the non-image data, to calculate a third feature amount in which the first feature amount and the second feature amount are fused, and predicts an aspect related to the matter at a time different from a time when the image data is captured on the basis of the third feature amount.

According to yet still another aspect of the present disclosure, there is provided a program that causes a computer to implement: a function of receiving an input of image data and non-image data related to a target matter; a function of performing weighting calculation by a calculation method, which outputs a combination of products of elements of a first feature amount calculated from the image data and a second feature amount calculated from the non-image data, to calculate a third feature amount in which the first feature amount and the second feature amount are fused; and a function of predicting an aspect related to the matter at a time different from a time when the image data is captured on the basis of the third feature amount.

According to still yet another aspect of the present disclosure, there is provided a trained model that has been subjected to machine learning so as to receive an input of image data and non-image data related to a target matter and to output information predicted from the image data and the non-image data. The trained model causes a computer to execute: performing weighting calculation by a calculation method, which outputs a combination of products of elements of a first feature amount calculated from the image data and a second feature amount calculated from the non-image data, to calculate a third feature amount in which the first feature amount and the second feature amount are fused; and outputting the information indicating the aspect related to the matter at a time different from a time when the imaging data is captured on the basis of the third feature amount.

In the trained model according to yet still another aspect of the present disclosure, the target matter may be a health condition of a subject, the image data may be a medical image obtained by imaging the subject, the non-image data may include biological information of the subject, and the trained model may predict the health condition of the subject after a lapse of a specific period from a time when the medical image is captured or the health condition of the subject at a past time before a specific period from the time when the medical image is captured.

According to still yet another aspect of the present disclosure, there is provided a diagnostic support device comprising: a non-transitory computer-readable medium on which the trained model according to an aspect of the present disclosure is recorded; and a processor that operates according to the trained model.

According to yet still another aspect of the present disclosure, there is provided a learning device comprising: a processor; and a non-transitory computer-readable medium on which a learning program executed by the processor is recorded. According to commands of the learning program, the processor acquires learning data including image data and non-image data related to a target matter and data indicating a known aspect of the matter corresponding to a combination of the image data and the non-image data, inputs the image data and the non-image data to the learning model, and performs machine learning on the learning model using the image data and the non-image data such that prediction information indicating an aspect related to the matter at a time different from a time when the image data is captured is output. The learning model performs weighting calculation by a calculation method, which outputs a combination of products of elements of a first feature amount calculated from the image data and a second feature amount calculated from the non-image data, to calculate a third feature amount in which the first feature amount and the second feature amount are fused, and outputs the prediction information on the basis of the third feature amount.

According to still yet another aspect of the present disclosure, there is provided a prediction model generation method comprising: acquiring learning data including image data and non-image data related to a target matter and data indicating a known aspect of the matter corresponding to a combination of the image data and the non-image data; and performing machine learning on the learning model using the learning data to generate a trained prediction model that outputs prediction information indicating an aspect related to the matter at a time different from a time when the image data is captured in response to an input of the image data and the non-image data. The learning model performs weighting calculation by a calculation method, which outputs a combination of products of elements of a first feature amount calculated from the image data and a second feature amount calculated from the non-image data, to calculate a third feature amount in which the first feature amount and the second feature amount are fused, and outputs the prediction information on the basis of the third feature amount.

A prediction model generation method is understood as an invention of a method for manufacturing a prediction model.

According to the invention, it is possible to accurately predict an aspect at a time different from the time when the image data is captured using the image data and the non-image data.

DESCRIPTION OF THE PREFERRED EMBODIMENTS

Hereinafter, preferred embodiments of the invention will be described in detail with reference to the accompanying drawings.

Outline of Embodiment

Figure 1:
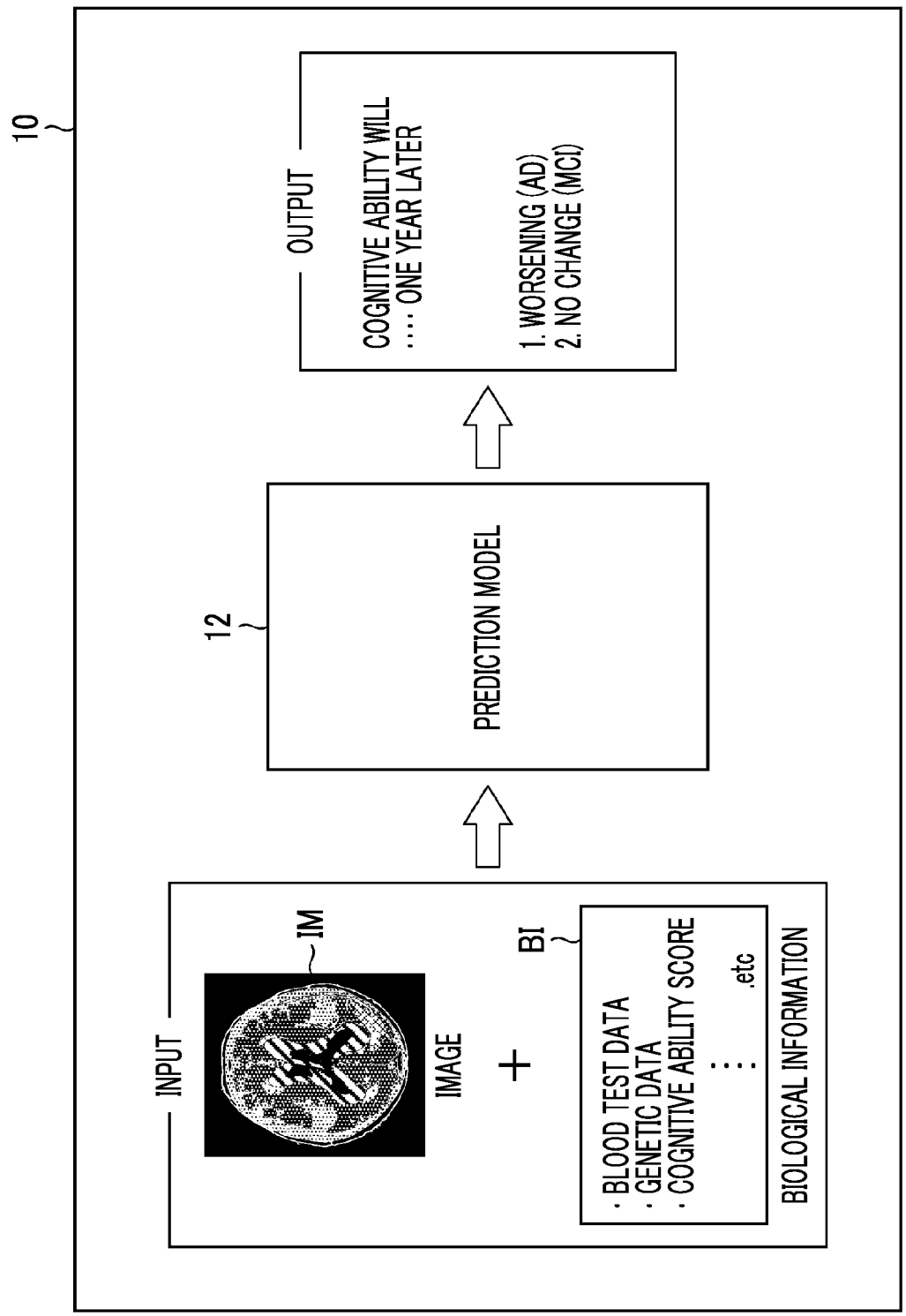
FIG. 1 is a diagram illustrating an outline of a process of an information processing device according to an embodiment of the invention.

FIG. 1 is a diagram illustrating an outline of a process of an information processing device 10 according to an embodiment of the invention. The information processing device 10 is a computer system that performs a dementia progression prediction task of predicting whether or not a patient with mild cognitive impairment (MCI) will progress to Alzheimer's disease (AD) one year after a baseline. In addition, the Alzheimer's disease is synonymous with Alzheimer-type dementia.

The information processing device 10 performs arithmetic processing using a trained prediction model 12 generated by machine learning. The prediction model 12 is, for example, a learning model that is constructed using a hierarchical multi-layer neural network, and parameters of the network are determined by deep learning. The parameters of the network include filter coefficients (weights for the connection between nodes) of filters used for processing in each layer and the bias of the nodes. In addition, the "neural network" is a mathematical model of information processing that simulates a mechanism of a cranial nervous system. Processing using the neural network can be implemented by a computer. A processing unit including the neural network can be configured as a program module.

The prediction model 12 is a class classification network that receives the input of an MRI image IM of the brain of the patient who is a subject and biological information BI of the patient, performs a two-class classification process of determining whether a target patient will change from MCI to Alzheimer's disease (AD) one year later, and outputs the determination result. The prediction model 12 can be understood as a class classifier and may be understood as a classifier or a discriminator that identifies a class.

The biological information BI includes, for example, at least one of blood test data, genetic data, a cognitive ability score, cerebrospinal fluid data, age, or gender and preferably includes a plurality of combinations thereof. It is preferable to use at least one of the blood test data, the genetic data, the cognitive ability score, or the cerebrospinal fluid data, the age, and the gender as the biological information BI. In this example, the blood test data, the genetic data, cognitive ability score, the age, and the gender are used as the biological information BI to be input to the information processing device 10. Further, in addition to the data described above as an example, data, such as other biomarkers having a correlation with MCI and Alzheimer's disease, may be used as the biological information BI.

The prediction model 12 performs the determination of two-class classification on the basis of a third feature amount obtained by fusing a first feature amount calculated from the input MRI image IM and a second feature amount calculated from the input biological information BI using a bilinear method. The "bilinear method" described here is a calculation method that calculates a combination of the products of elements of two different types of features using the first feature amount and the second feature amount.

The baseline in the prediction of the progression of dementia is, for example, a state at the time when a target person who is a patient is diagnosed. Specifically, the baseline is a state in a case in which the capture of the MRI image IM used for diagnosis and various tests, such as a cognitive ability test, are performed to acquire data. In addition, "one year later" described here may not be strict and may be approximately one year later, including a period range that is generally allowed. The time when the MRI image IM is captured or the time of the baseline when a test including the capture of the MRI image IM is performed is an example of the "time when the image data is captured" in the present disclosure. "One year later" is an example of "a time different from the time when the image data is captured" and "after a lapse of a specific period from the time when the image data is captured" in the present disclosure.

«Description of Learning Method»

A learning method for generating the prediction model 12 will be described.

[For Usage Data]

Data used for learning is, for example, data of an MCI patient having data of a plurality of types of items described below and is patient data capable of specifying whether or not the patient actually progressed to Alzheimer's disease one year later. In the case of this example, the data of the plurality of types of items includes MRI image data, blood test data, genetic data, cognitive ability score data, age data, and gender data.

The cognitive ability score may be, for example, any one of an Alzheimer's Disease Assessment Scale (ADAS) score, a Mini Mental State Examination (MMSE) score, a Functional Activities Questionnaire (FAQ) score, or a Clinical Dementia Rating (CDR) score, or a plurality of combinations of these. In a case in which learning is performed, the numerical value of a predetermined specific cognitive ability score is used.

The genetic data may be, for example, data indicating a genotype and specifically may be test data of apolipoprotein E (ApoE). ApoE is a gene involved in the development of Alzheimer's disease. The ApoE gene has three subtypes (ε2, ε3, and ε4), and a person having "ε4" among them has a relatively high risk of developing Alzheimer's disease.

A plurality of types of data including an MRI image and biological information are used as data input to the learning model. In addition, information indicating whether or not the MCI patient actually progressed to Alzheimer's disease one year later is used as correct label data (correct answer data)

indicating a known aspect corresponding to the input data. The correct answer data plays the role of a training signal in supervised learning.

Data of a plurality of MCI patients corresponding to the conditions of the usage data is used as a learning data set. The following preprocessing is performed on data used for learning in order to efficiently perform learning.

[For Preprocessing]

The normalization of a brightness value and registration with an atlas image are performed on the MRI image to facilitate learning. In addition, instead of the registration with the atlas image, registration with a standard brain may be performed.

The biological information is normalized to a numerical value from 0 to 1 within the range of the minimum and maximum values of the data set for each type of data. For the genotype, a type that has "ε4" is input as "1", and a type that does not have "ε4" is input as "0".

The above-mentioned preprocessing may be performed by a learning device into which a learning program for performing machine learning has been incorporated or may be performed by a computer system different from the learning device.

[Network Structure of Learning Model]

Figure 2:
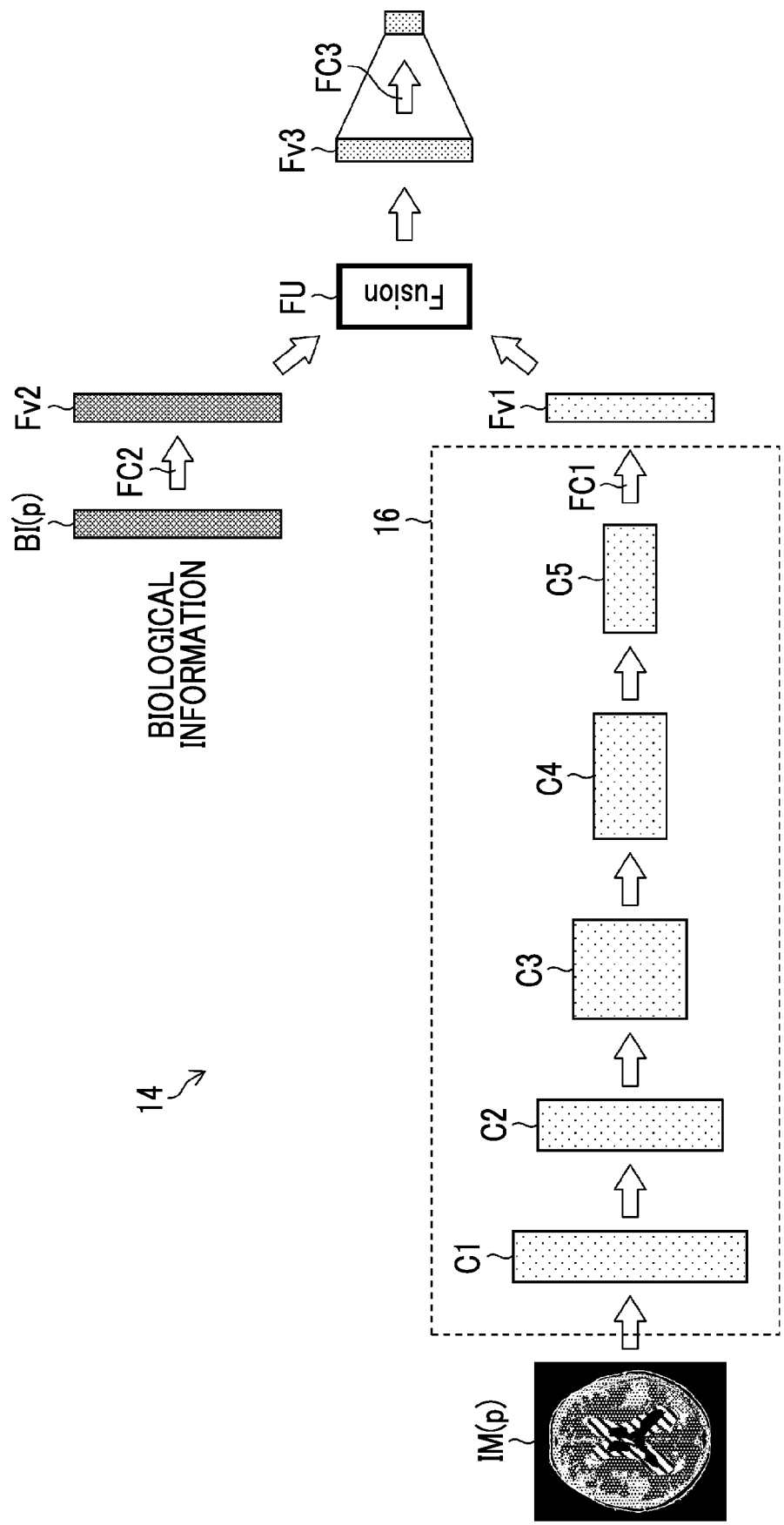
FIG. 2 is a conceptual diagram illustrating a network structure of a learning model used for machine learning for generating a prediction model.

FIG. 2 is a conceptual diagram illustrating the network structure of a learning model 14 that is used for machine learning for generating the prediction model 12. Deep learning is performed using the learning model 14 to determine the parameters of the network. The network structure illustrated in FIG. 2 may be understood as the network structure of the prediction model 12.

In FIG. 2, an MRI image IM(p) and biological information BI(p) are input data for learning, and "p" indicates an index of the learning data. The learning model 14 comprises: a neural network 16 including a plurality of convolutional layers and a fully connected layer FC1 that calculate a first feature amount Fv1 from the input MRI image IM(p); a fully connected layer FC2 that calculates a second feature amount Fv2 from the input biological information BI(p); a fusion layer FU that fuses the first feature amount Fv1 and the second feature amount Fv2 using weighting calculation by the bilinear method; and a fully connected layer FC3 that calculates a final output value from a third feature amount Fv3 obtained from the fusion layer FU.

Each of blocks represented by reference numerals C1, C2, C3, C4, and C5 in FIG. 2 indicates a network module obtained by putting the arithmetic processing of a plurality of layers into one block. In the case of this example, one block indicates a network module including a plurality of layers in which a convolution process, a batch normalization process, a rectified linear unit (ReLU) function, a convolution process, a batch normalization process, a ReLU function, and a pooling process are performed in this order.

In FIG. 2, the size of each block in the vertical direction gradually decreases from C1 to C5, which shows that the image size of a feature map calculated in each block gradually decreases. In addition, the size of each block in the horizontal direction indicates a relative change in the number of channels of the feature map calculated in each block.

The outline of the process by the learning model 14 is as follows. That is, the MM image IM(p) passes through a plurality of convolutional layers to extract the first feature amount Fv1. The first feature amount Fv1 is represented by a vector including a plurality of elements. The fully connected layer FC2 performs one full connection process on the biological information BI(p) to obtain the second feature amount Fv2. The second feature amount Fv2 is represented by a vector including a plurality of elements. Then, the fusion layer FU fuses the first feature amount Fv1 and the second feature amount Fv2, and the fully connected layer FC3 calculates a final output value using the fused third feature amount Fv3.

Since the learning model 14 according to this example performs the determination of two-class classification, the final output value obtained from the fully connected layer FC3 may be, for example, a classification score indicating the certainty (likelihood) of each class. The classification score may be converted into a value normalized to a numerical value in the range of 0 to 1, that is, a probability by, for example, a softmax function.

The neural network 16 illustrated in FIG. 2 is an example of a "first processing unit" and a "first neural network" according to the present disclosure. The fully connected layer FC1 is an example of a "first fully connected layer" according to the present disclosure. The fully connected layer FC2 is an example of a "second processing unit", a "second fully connected layer", and a "second neural network" according to the present disclosure. The fusion layer FU is an example of a "third processing unit" according to the present disclosure. The fully connected layer FC3 is an example of a "third fully connected layer" according to the present disclosure. Each of the fully connected layers FC1, FC2, and FC3 may be configured to include a plurality of layers. The final output value obtained through the fully connected layer FC3 is an example of "prediction information" according to the present disclosure.

Figure 3:
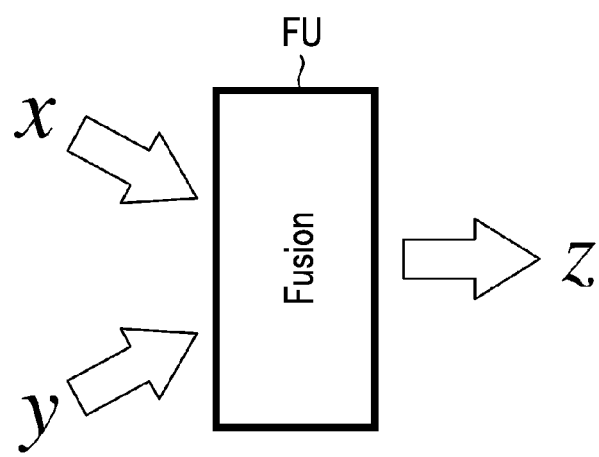
FIG. 3 is a diagram illustrating an outline of weighting calculation using a bilinear method.

FIG. 3 is a diagram illustrating the outline of the weighting calculation using the bilinear method in the fusion layer FU. In FIG. 3, x indicates the first feature amount obtained from the MRI image IM(p), and y indicates the second feature amount obtained from the biological information BI(p). In addition, z indicates the third feature amount output from the fusion layer FU. As illustrated in FIG. 3, the fusion process using the bilinear method multiplies elements of x and y, weights the products thereof, and adds the weighted values. That is, elements of z are calculated according to the following Expression 1.

$$z_k = \sum_{ij} w_{ijk} x_i y_j \qquad \text{(Expression 1)}$$

In the expression, i is an index of the element of x. j is an index of the element of y. k is an index of the element of z.

As illustrated in Expression 1, the fusion layer FU performs weighting calculation by a calculation method, which outputs a combination of the products of elements of two different types of feature amounts, using the first feature amount and the second feature amount to generate the third feature amount in which the two types of feature amounts have been fused.

For comparison, a numerical expression of a connection process by linear connection (linear method) is shown below.

$$z_k = \sum_{i} w_{ik} x_i + \sum_{j} w_{jk} y_j \qquad \text{(Expression 2)}$$

As illustrated in Expression 2, the connection process by the linear method weights each of the elements of x and y and adds the weighted values. In the linear method, it is difficult to consider a combination of the products of the elements of x and y.

Therefore, in the fusion process using the bilinear method represented by Expression 1, since the combination of the products of the elements of x and y is considered, the expressive power of the network is improved. In addition, since the product of the elements also includes the meaning of correlation, the accuracy of prediction can be improved by considering the correlation between two feature amounts obtained from different types of information.

The calculation method in the fusion layer FU is not limited to the bilinear method represented by Expression 1. For example, a bilinear shake method may be applied. In the bilinear shake method, the weighting of each element in the calculation of the product of two types of feature amounts is changed by a random number.

Figure 4:
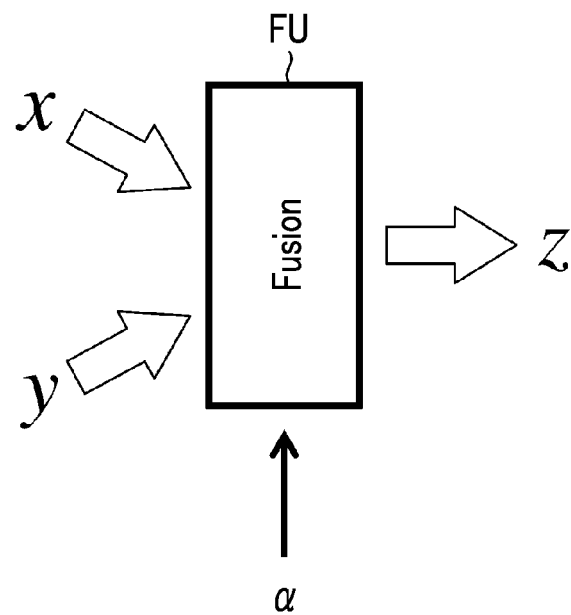
FIG. 4 is a diagram illustrating an outline of weighting calculation using a bilinear shake method.

FIG. 4 is a diagram illustrating the outline of weighting calculation using the bilinear shake method in the fusion layer FU. In FIG. 4, x indicates the first feature amount obtained from the MRI image IM(p), and y indicates the second feature amount obtained from the biological information BI(p). a indicates a value of 0 to 1 generated by a random number. a is generated for each element k, i, or j. z indicates the third feature amount output from the fusion layer FU. As illustrated in FIG. 4, the fusion process using the bilinear shake method multiplies the elements of x and y, weights the products thereof, and adds the weighted values. That is, the elements of z are calculated according to the following Expression 3.

$$z_k = \sum_{ij} w_{ijk} \{\alpha(x_i - 1) + 1\}\{(\alpha - 1)(y_j - 1) + 1\} \quad \text{(Expression 3)}$$

In the expression, i is an index of the element of x. j is an index of the element of y. k is an index of the element of z.

As illustrated in Expression 3, the fusion layer FU performs weighting calculation by a calculation method, which outputs a combination of the products of elements of two different types of feature amounts, using the first feature amount and the second feature amount to generate the third feature amount in which the two types of feature amounts have been fused.

In the bilinear shake method, a combination of the products is considered at a random ratio for the first feature amount and the second feature amount, as compared to the bilinear method. Therefore, it is possible to prevent learning from being biased to one of the feature amounts.

For α, the following aspect can be considered as a random number generation pattern. For example, in a case in which it is considered that there are 10 combinations of x and y as learning data and they are trained for 10 epochs, the following three patterns are considered as the random number generation patterns of α.

[Pattern 1] A random number is generated for each combination of x and y. In this case, for example, in the first epoch and the second epoch, a used for each combination of (x, y) is the same.

[Pattern 2] A random number is generated for each epoch. In this case, in the same epoch, a is the same regardless of the combination of (x, y).

[Pattern 3] A random number is generated for each combination of x and y and for each epoch. In this case, the same a is not present.

«Example of Configuration of Medical Image Information System»

Figure 5:
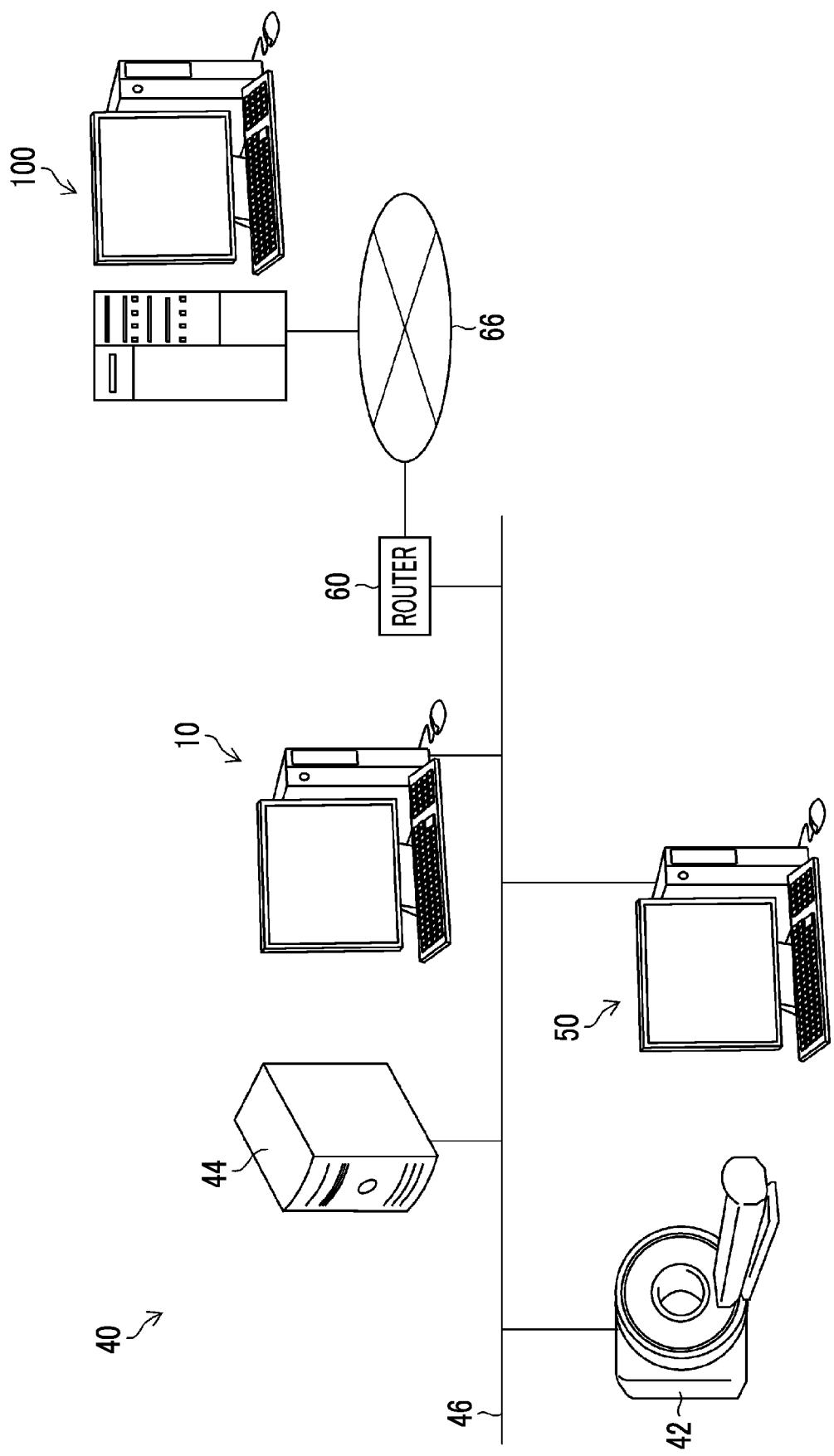
FIG. 5 is a hardware configuration diagram illustrating an outline of a medical image information system including the information processing device according to the embodiment of the invention.

FIG. 5 is a hardware configuration diagram illustrating the outline of a medical image information system 40 including the information processing device 10 according to the embodiment of the invention. In the medical image information system 40, a three-dimensional imaging apparatus 42, an image storage server 44, and the information processing device 10 are connected through a communication line 46 such that they can communicate with each other. The communication line 46 may be, for example, a local area network that is constructed in a medical institution such as a hospital. The form of connection to the communication line 46 and communication between devices is not limited to a wired system and may be a wireless system.

The three-dimensional imaging apparatus 42 is an apparatus that captures an image of a diagnosis target part of a patient who is a subject to generate a three-dimensional image indicating the part and is specifically a CT apparatus, an MRI apparatus, a PET apparatus, or the like. The three-dimensional image which consists of a plurality of slice images and has been generated by the three-dimensional imaging apparatus 42 is transmitted and stored in the image storage server 44 for each unit examination.

In this embodiment, the diagnosis target part of the patient is the brain, and the three-dimensional imaging apparatus 42 is an MRI apparatus. Then, the MRI apparatus generates a three-dimensional MRI image including the brain of the patient. In this embodiment, the MM image is a diffusion-weighted image.

FIG. 5 illustrates one three-dimensional imaging apparatus 42. However, a plurality of three-dimensional imaging apparatuses may be connected to the communication line 46. In addition, the plurality of three-dimensional imaging apparatuses may include different modalities.

The image storage server 44 is a computer that stores and manages various types of data and comprises a high-capacity external storage device and database management software. The image storage server 44 communicates with other devices through the communication line 46 to transmit and receive, for example, image data.

Specifically, the image storage server 44 acquires various types of data including the image data of the three-dimensional image generated by the three-dimensional imaging apparatus 42 through the communication line 46, stores the acquired data in a recording medium, such as a high-capacity external storage device, and manages the data. In addition, the storage format of the image data and the communication between the devices through the communication line 46 are based on a protocol such as Digital Imaging and Communication in Medicine (DICOM).

The image storage server 44 stores biological information including blood test data, genetic data, a cognitive ability score, and the age and gender of the patient in addition to the image data. In addition to the information processing device 10, an in-hospital terminal device 50 may be connected to the communication line 46. FIG. 5 illustrates one in-hospital terminal device 50. However, a plurality of in-hospital terminal devices may be connected to the communication line 46. The biological information including the blood test data and other test data can be input from the information processing device 10 and/or the in-hospital terminal device 50. The biological information can be transmitted from the information processing device 10 and/or the in-hospital terminal device 50 to the image storage server 44. In addition, the functions of the information processing device 10 may be incorporated into the in-hospital terminal device 50.

The communication line 46 may be connected to a wide area communication network 66 through a router 60. The wide area communication network 66 may be configured to include the Internet and/or a dedicated communication line.

A learning device 100 is configured by a computer system in order to generate the prediction model 12 incorporated into the information processing device 10. The learning device 100 is connected to the wide area communication network 66 and can collect learning data through the wide area communication network 66. The learning device 100 can collect learning data from a plurality of image storage servers installed in a plurality of medical institutions (not illustrated in FIG. 5) in addition to the image storage server 44. Further, in a case in which the learning device 100 provides the learning data to the image storage server 44 or the like, personal information, such as a name that can specify an individual patient, is kept secret.

A learning data set which is a group of a plurality of learning data items, is stored in a storage provided in the learning device 100, an external storage connected to the learning device 100, a data storage server, or the like.

«Example of Configuration of Learning Device 100»

Figure 6:
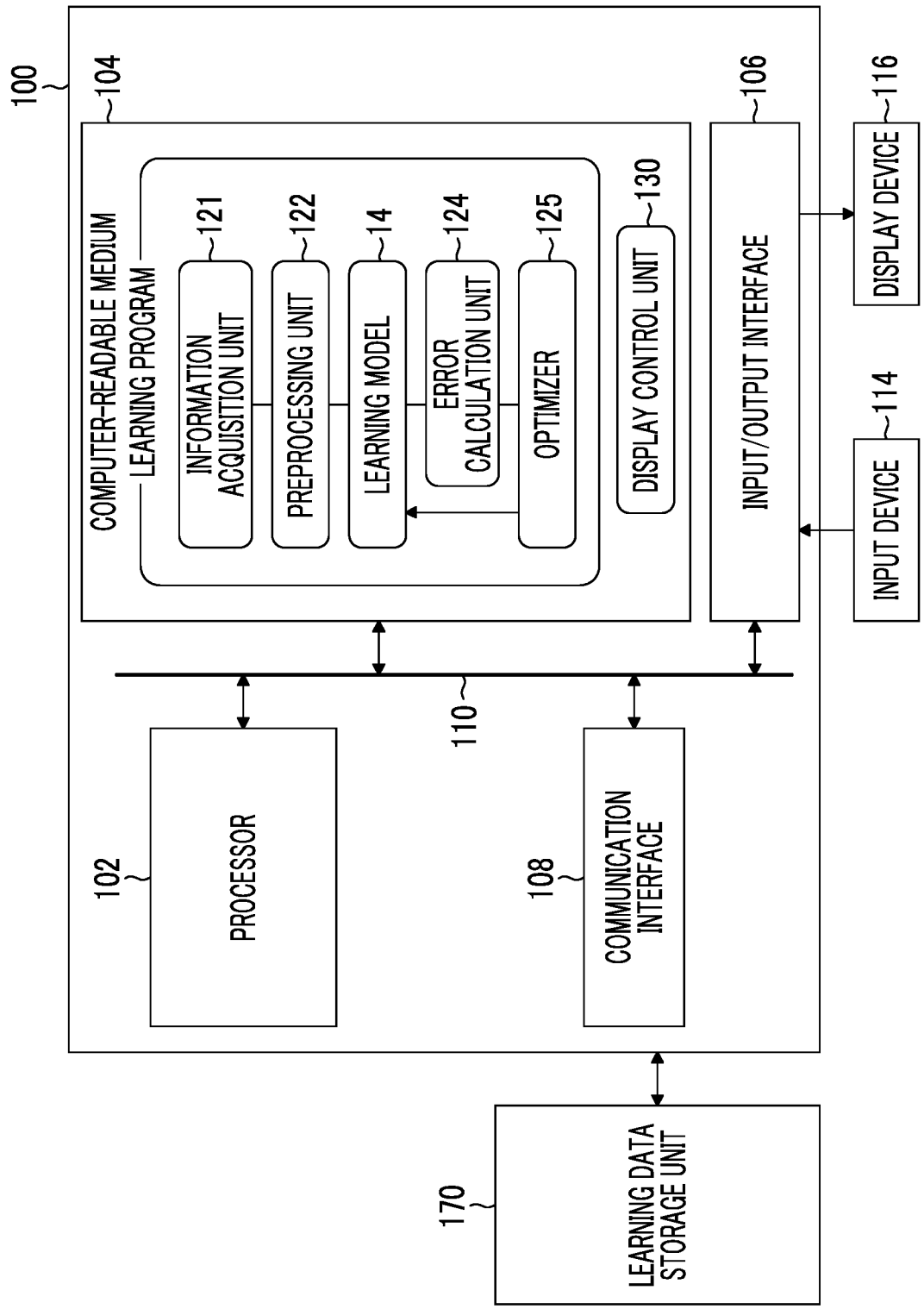
FIG. 6 is a block diagram illustrating a schematic configuration of a learning device.

FIG. 6 is a block diagram illustrating the schematic configuration of the learning device 100. The learning device 100 can be implemented by a computer system configured using one or a plurality of computers. The computer system constituting the learning device 100 may be the same as or different from the computer system constituting the information processing device 10 or may share some elements with the computer system constituting the information processing device 10.

The learning device 100 is implemented by installing a learning program in a computer. The learning device 100 comprises a processor 102, a non-transitory computer-readable medium 104, an input/output interface 106, a communication interface 108, a bus 110, an input device 114, and a display device 116. The processor 102 includes a CPU. The processor 102 may include a GPU. The processor 102 is connected to the computer-readable medium 104, the input/output interface 106, and the communication interface 108 through the bus 110.

The computer-readable medium 104 includes a memory which is a main storage device and a storage which is an auxiliary storage device. The computer-readable medium 104 may be a semiconductor memory, a hard disk drive (HDD) device, a solid state drive (SSD) device, or a plurality of combinations thereof.

The learning device 100 is connected to a learning data storage unit 170 through the communication interface 108 or the input/output interface 106. The learning data storage unit 170 is configured to include a storage that stores learning data necessary for the learning device 100 to perform machine learning. The "learning data" is training data used for machine learning and is synonymous with "data for learning" or "training data".

Here, an example in which the learning data storage unit 170 and the learning device 100 are configured as separate devices is described. However, the functions of the learning data storage unit 170 and the learning device 100 may be implemented by one computer, or the functions of the processes may be dispersedly implemented by two or more computers.

Various programs including the learning program and data are stored in the computer-readable medium 104. The learning program is a program that implements a function of causing the computer to train the learning model 14. The processor 102 executes a command of the learning program such that the computer functions as an information acquisition unit 121, a preprocessing unit 122, a learning model 14, an error calculation unit 124, and an optimizer 125.

The information acquisition unit 121 acquires learning data from the learning data storage unit 170. The information acquisition unit 121 may be configured to include a data input terminal for acquiring data from the outside or other signal processing unit in the device. Further, the information acquisition unit 121 may be configured to include the input/output interface 106, the communication interface 108, a media interface that performs reading and writing on a portable external storage medium, such as a memory card (not illustrated), or an appropriate combination of these aspects. In addition, the information acquisition unit 121 can acquire data necessary for executing learning data from the image storage server 44 illustrated in FIG. 5.

The preprocessing unit 122 performs preprocessing for improving the efficiency of a machine learning process on the MRI image and the biological information acquired from, for example, the image storage server 44. The learning data processed by the preprocessing unit 122 can be stored in the learning data storage unit 170. In addition, in a case in which a learning data set subjected to necessary preprocessing is prepared in advance, it is possible to omit the process of the preprocessing unit 122.

The error calculation unit 124 calculates an error between a predicted value indicated by the classification score output from the learning model 14 and correct answer data. The error calculation unit 124 evaluates the error using a loss function. The loss function may be, for example, cross entropy or a mean square error.

The optimizer 125 performs a process of updating the parameters of the network in the learning model 14 from the calculation result of the error calculation unit 124.

Further, in a case in which the processor 102 executes a command of a display control program such that the computer functions as a display control unit 130. The display control unit 130 generates a display signal necessary for display output to the display device 116 and controls the display of the display device 116.

The input device 114 is composed of, for example, a keyboard, a mouse, a touch panel, other pointing device, a voice input device, or an appropriate combination thereof. The input device 114 receives various inputs from an operator. The display device 116 is composed of, for example, a liquid crystal display, an organic electro-luminescence (OEL) display, a projector, or an appropriate combination thereof. The input device 114 and the display device 116 are connected to the bus 110 through the input/output interface 106. In addition, a touch panel may be used such that the display device 116 and the input device 114 are integrated.

«Example of Learning Data»

Figure 7:
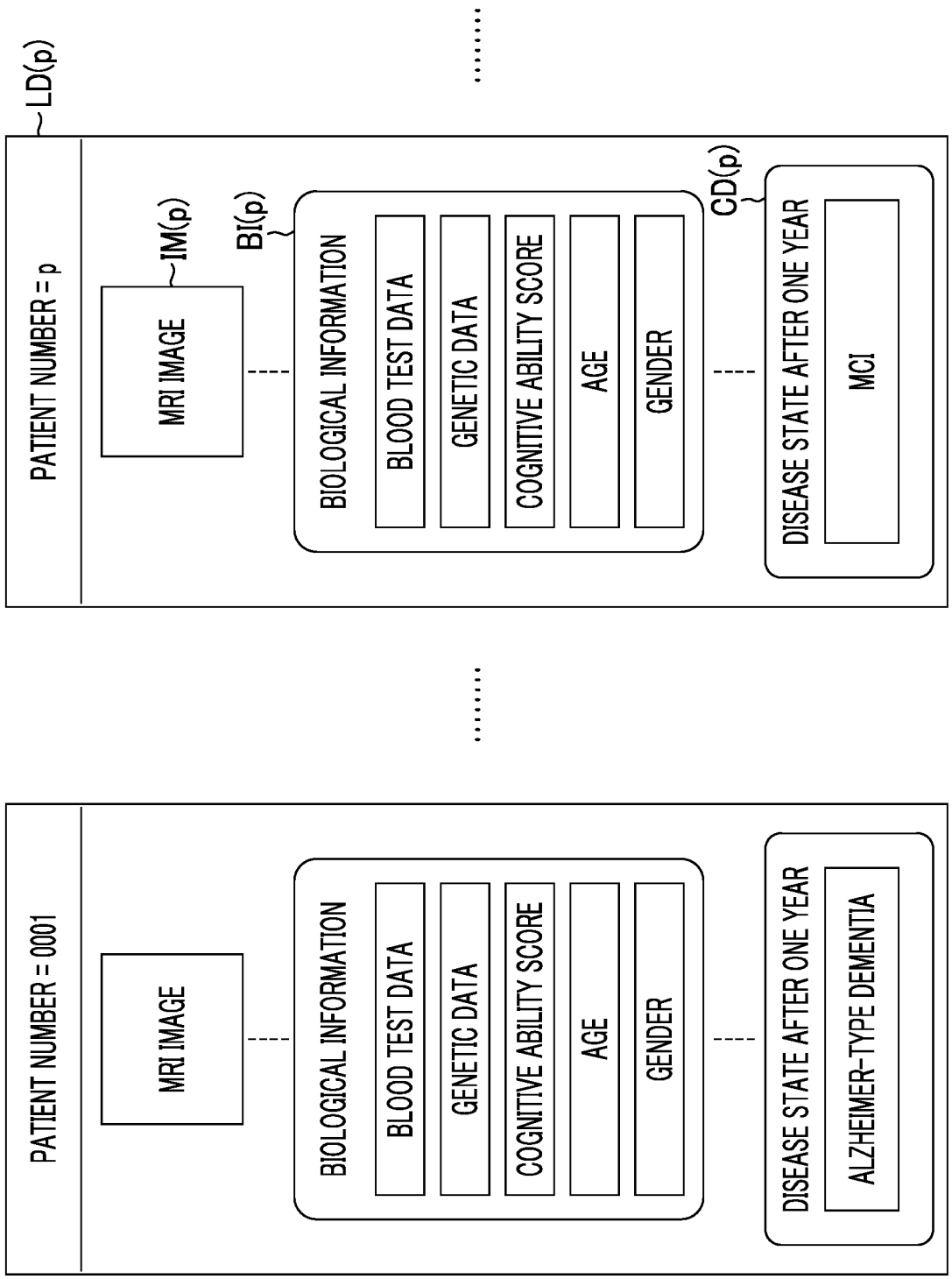
FIG. 7 is a conceptual diagram illustrating learning data stored in a learning data storage unit.

FIG. 7 is a conceptual diagram illustrating the learning data stored in the learning data storage unit 170. The learning data storage unit 170 stores learning data LD(p) in which a combination of the MRI images IM(p), the biological information BI(p), and correct answer information CD(p), which is known information indicating a disease state after one year, for a plurality of MCI patients is associated with each patient. The MRI image IM(p) may be preprocessed image data that has been preprocessed. p indicates, for example, an index corresponding to a patient number.

«Description of Functions of Learning Device 100»

Figure 8:
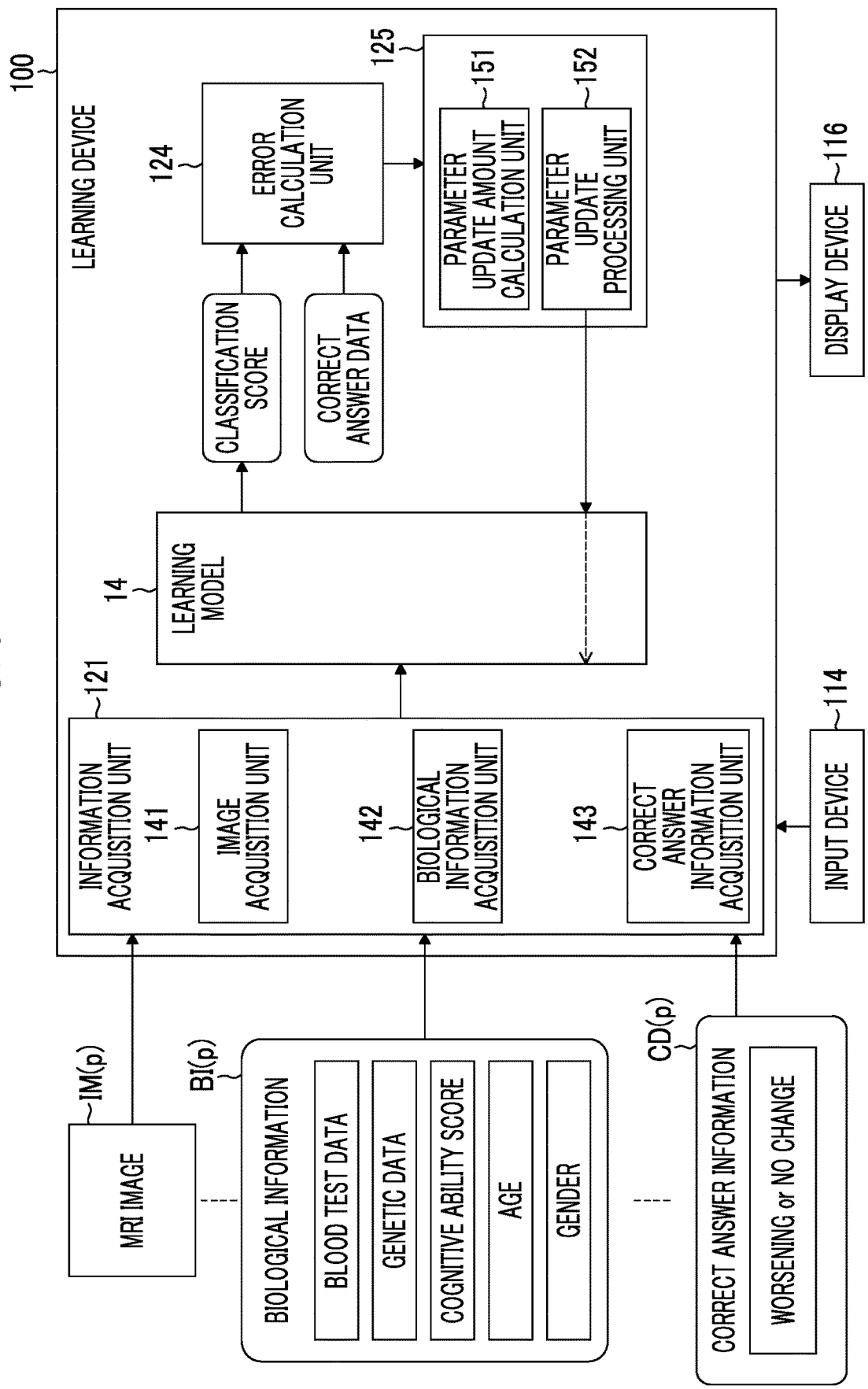
FIG. 8 is a functional block diagram illustrating the functions of a learning process in the learning device.

FIG. 8 is a functional block diagram illustrating the function of the learning process in the learning device 100. In FIG. 8, the same elements as those in FIG. 6 are denoted by the same reference numerals. The learning device 100 reads the learning data LD(p) from the learning data storage unit 170 and performs machine learning. The learning device 100 can perform the reading of the learning data LD(p) and the update of the parameters in units of mini-batches each of which is a group of a plurality of learning data items LD(p).

FIG. 8 illustrates the flow of the processing of one set of learning data. In a case in which mini-batch learning is performed, a plurality of sets (for example, m sets) of learning data included in a mini-batch are collectively processed. The information acquisition unit 121 of the learning device 100 includes an image acquisition unit 141, a biological information acquisition unit 142, and a correct answer information acquisition unit 143. The image acquisition unit 141 acquires the MRI image IM(p). The biological information acquisition unit 142 acquires the biological information BI(p). The correct answer information acquisition unit 143 acquires the correct answer information CD(p). The correct answer information CD(p) is, for example, classification score data (correct answer data) indicating the correct answer label of the class classification. In the case of two-class classification, specifically, a score for Alzheimer's disease can be set as "1", and a score for MCI can be set as "0".

The MRI image IM(p) acquired through the image acquisition unit 141 is input to the learning model 14. The biological information BI(p) acquired through the biological information acquisition unit 142 is input to the learning model 14. The learning model 14 outputs a classification score corresponding to the class according to the process described with reference to FIGS. 2 and 3 or the process described with reference to FIGS. 2 and 4. The classification score calculated by the learning model 14 corresponds to a predicted value.

The error calculation unit 124 performs calculation for evaluating an error between the classification score output from the learning model 14 and the correct answer data acquired from the correct answer information acquisition unit 143.

The optimizer 125 includes a parameter update amount calculation unit 151 and a parameter update processing unit 152. The parameter update amount calculation unit 151 calculates the amount of update of the parameters of the network in the learning model 14 using the calculation result of the error obtained from the error calculation unit 124. The parameter update processing unit 152 performs a process of updating the parameters of the learning model 14 according to the amount of update of the parameters calculated by the parameter update amount calculation unit 151. The optimizer 125 updates the parameters on the basis of an algorithm such as a backpropagation method.

The parameters to be updated include the parameters of the neural network 16 including a plurality of convolutional layers and the fully connected layer FC1, the weighting parameters of the fully connected layer FC2, the weighting parameters of the fusion layer FU, and the weighting parameters of the fully connected layer FC3. In addition, some of the parameters of the neural network 16 may be excluded from the update target. For example, among the blocks represented by C1 to C5 in FIG. 2, some parameters of the layer close to the input side may be fixed.

«Example of Learning Method Using Learning Device 100»

Figure 9:
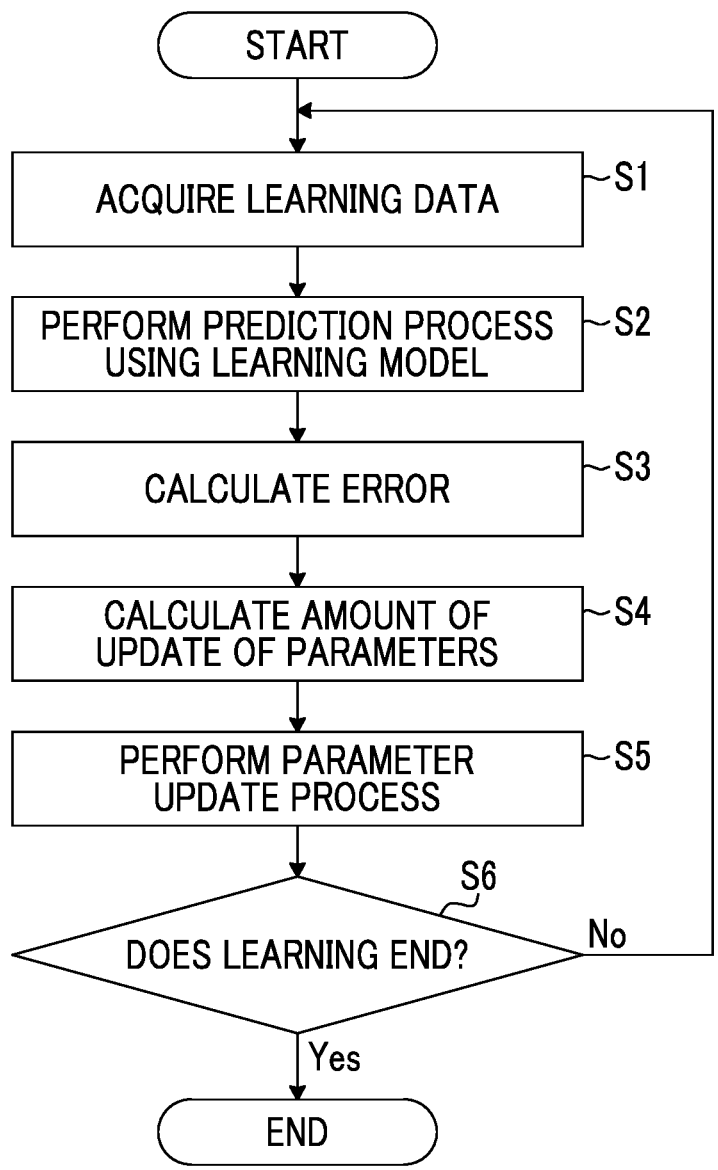
FIG. 9 is a flowchart illustrating a procedure of a learning method using the learning device.

FIG. 9 is a flowchart illustrating an example of the procedure of the learning method using the learning device 100. A learning data set is prepared as a preliminary preparation before the learning process is performed. That is, a plurality of learning data items which are combinations of the MRI images IM(p), the biological information BI(p), and the correct answer information CD(p) described with reference to FIG. 7 are prepared. The function of generating the learning data sets may be incorporated into the learning device 100 or may be incorporated into a device other than the learning device 100.

In Step S1 of FIG. 9, the learning device 100 acquires the learning data. The learning device 100 can acquire a plurality of learning data items in units of mini-batches from the learning data storage unit 170.

In Step S2, the learning device 100 inputs the MRI image and the biological information to the learning model 14 and performs the prediction process using the learning model 14. As described with reference to FIG. 2, the prediction process performed by the learning model 14 includes a process of calculating the first feature amount Fv1 from the MRI image, a process of calculating the second feature amount Fv2 from the biological information, a process of fusing the first feature amount Fv1 and the second feature amount Fv2 using the weighting calculation by the bilinear method to calculate the third feature amount Fv3, and a process of calculating a predicted value on the basis of the third feature amount Fv3.

In Step S3, the error calculation unit 124 calculates an error between the predicted value obtained from the learning model 14 and the correct answer data.

In Step S4, the optimizer 125 calculates the amount of update of the parameters of the learning model 14 on the basis of the error calculated in Step S3.

In Step S5, the optimizer 125 updates the parameters of the learning model 14 according to the amount of update calculated in Step S4. The parameter update process is performed in units of mini-batches.

In Step S6, the learning device 100 determines whether or not to end learning. Learning end conditions may be determined on the basis of the value of the error or may be determined on the basis of the number of times the parameters are updated. As a method based on the value of the error, for example, the learning end condition may be that the error falls within a prescribed range. As a method based on the number of updates, for example, the learning end condition may be that the number of updates reaches a prescribed number of times.

In a case in which the determination result in Step S6 is "No", the learning device 100 returns to Step s1 and repeats the learning process until the learning end condition is satisfied. In a case in which the determination result in Step S6 is "Yes", the learning device 100 ends the flowchart illustrated in FIG. 9.

The trained learning model 14 obtained in this way is applied as the prediction model 12 of the information processing device 10. The learning method described with reference to FIG. 9 is an example of a method for generating the prediction model 12.

After generating the prediction model 12, the learning device 100 may perform additional learning using newly collected learning data to update the parameters of the prediction model 12. The trained parameters obtained by the additional learning can be provided to the information processing device 10 through the wide area communication network 66 or by a portable external storage medium such as a memory card. This configuration makes it possible to update the prediction performance of the prediction model 12.

«Example of Configuration of Information Processing Device 10»

Figure 10:
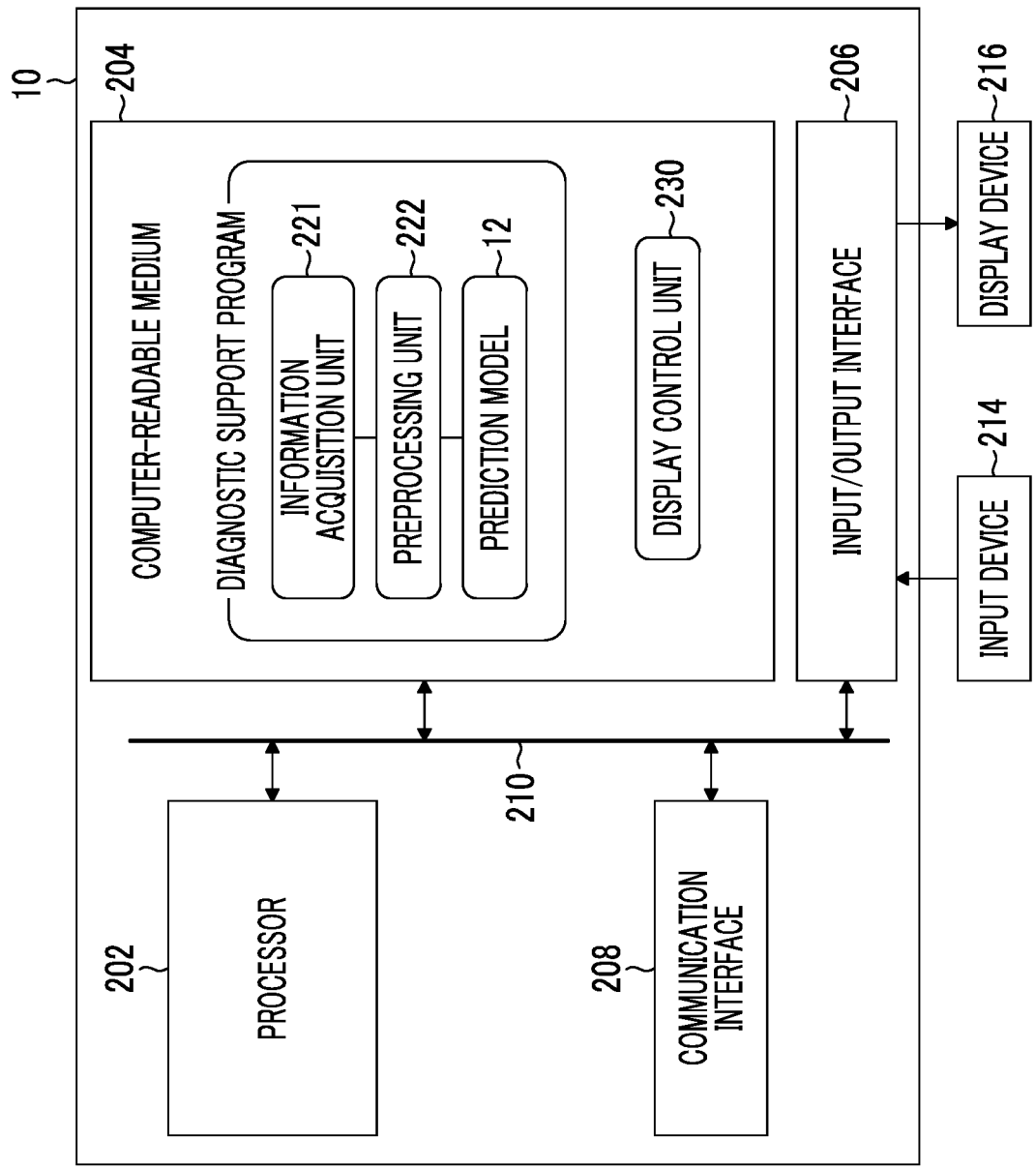
FIG. 10 is a block diagram illustrating a schematic configuration of an information processing device.

FIG. 10 is a block diagram illustrating the schematic configuration of the information processing device 10. The information processing device 10 is implemented by installing a diagnostic support program in the computer. The information processing device 10 comprises a processor 202, a non-transitory computer-readable medium 204, an input/output interface 206, a communication interface 208, a bus 210, an input device 214, and a display device 216. The hardware configuration of the information processing device 10 may be the same as the hardware configuration of the learning device 100 described with reference to FIG. 8. That is, the processor 202, the computer-readable medium 204, the input/output interface 206, the communication interface 208, the bus 210, the input device 214, and the display device 216 illustrated FIG. 10 have the same hardware configurations as the processor 102, the computer-readable medium 104, the input/output interface 106, the communication interface 108, the bus 110, the input device 114, and the display device 116 illustrated in FIG. 6, respectively.

The computer-readable medium 204 illustrated in FIG. 10 stores various programs including the diagnostic support program and data. The diagnostic support program is a program for predicting the progression of dementia on the basis of the MRI image and the biological information of the patient to be diagnosed. The processor 202 executes a command of the diagnostic support program such that the computer functions as an information acquisition unit 221, a preprocessing unit 222, and the prediction model 12.

Further, the processor 202 executes a command of a display control program such that the computer functions as a display control unit 230. The display control unit 230 generates a display signal necessary for display output to the display device 216 and controls the display of the display device 216.

The information acquisition unit 221 acquires the MRI image and the biological information of the patient who has undergone the examination. The information acquisition unit 221 can acquire data of the patient from the image storage server 44. The information acquisition unit 221 may be configured to include a data input terminal for acquiring data from the outside or other signal processing unit in the device. Further, the information acquisition unit 221 may be configured to include the input/output interface 206, the communication interface 208, a media interface that performs reading and writing on a portable external storage medium, such as a memory card (not illustrated), or an appropriate combination of these aspects.

The preprocessing unit 222 performs preprocessing on the MRI image and the biological information acquired through the information acquisition unit 221. The content of the process by the preprocessing unit 222 may be the same as that of the preprocessing unit 122 of the learning device 100.

The prediction model 12 predicts whether or not a target patient will progress to Alzheimer's disease one year later on the basis of the input MRI image and biological information according to the algorithm described with reference to FIG. 2. The problem of predicting the progress of "whether or not a patient will progress to Alzheimer's disease one year layer" is the same as the problem of "whether or not a patient will develop Alzheimer's disease within one year", that is, the problem of predicting whether the disease state of the patient after one year is Alzheimer's disease or MCI.

The disease state of the patient after one year is an example of "an aspect related to a matter at a time different from the time when the image data is captured" and a "health condition of a subject" according to the present disclosure. The prediction model 12 is an example of a "prediction unit" according to the present disclosure. Alzheimer's disease and MCI as candidates of the disease state after one year are an example of "a plurality of candidates of the aspect related to the matter at a time different from the time when the image data is captured" according to the present disclosure. Alzheimer's disease as a candidate of the disease state after one year is an example of a "first state" according to the present disclosure, and MCI as a candidate of the disease state after one year is an example of a "second state" according to the present disclosure.

«Description of Functions of Information Processing Device 10»

Figure 11:
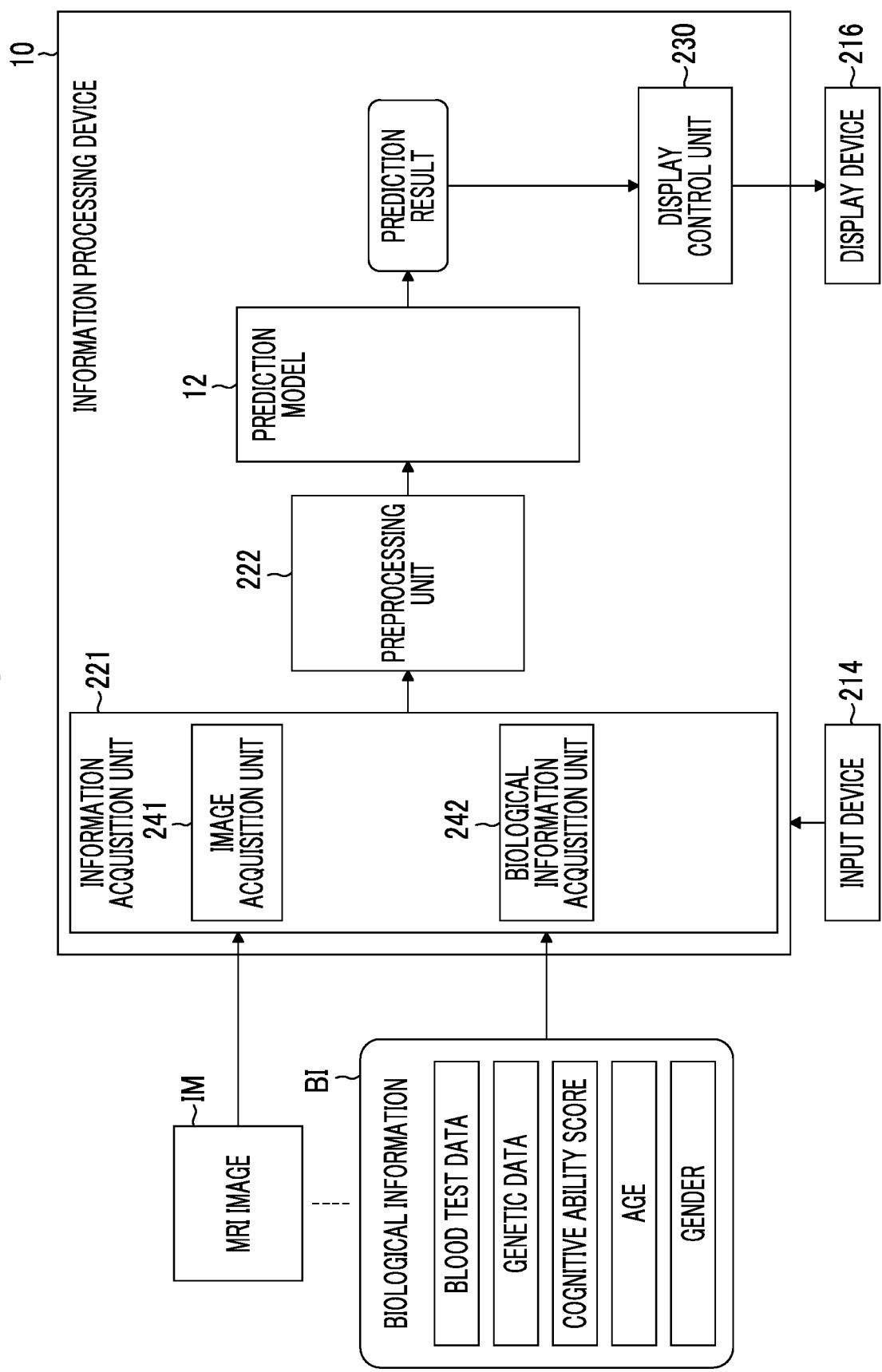
FIG. 11 is a functional block diagram illustrating the functions of a dementia progression prediction process in the information processing device.

FIG. 11 is a functional block diagram illustrating the function of a dementia progression prediction process in the information processing device 10. In FIG. 11, the same elements as those described with reference to FIG. 10 are denoted by the same reference numerals. The information processing device 10 reads the MRI image and biological information of an MCI patient who is a subject from, for example, the image storage server 44.

The information acquisition unit 221 of the information processing device 10 includes an image acquisition unit 241 and a biological information acquisition unit 242. The image acquisition unit 241 acquires an MRI image IM. The biological information acquisition unit 242 acquires biological information BI.

The MRI image IM acquired through the image acquisition unit 241 is preprocessed by the preprocessing unit 222 and is then input to the prediction model 12. In addition, the biological information BI acquired through the biological information acquisition unit 242 is preprocessed by the preprocessing unit 222 and is then input to the prediction model 12. Further, in a case in which the information acquisition unit 221 acquires the MRI image and the biological information that have been subjected to necessary preprocessing in advance, the preprocessing by the preprocessing unit 222 can be omitted.

The prediction model 12 outputs the prediction result according to the process described with reference to FIGS. 2 and 3 or the process described with reference to FIGS. 2 and 4. The prediction result is displayed on the display device 216 through the display control unit 230.

The information processing device 10 is an example of a "diagnostic support device" according to the present disclosure. The MRI image IM and the biological information BI of the MCI patient correlate with the progression of the disease state. The MRI image IM and the biological information BI are an example of "image data and non-image data related to a target matter" according to the present disclosure. The MRI image IM is an example of "image data" according to the present disclosure. The biological information BI is an example of "non-image data" according to the present disclosure. The prediction result output from the prediction model 12 is an example of a "result of a class classification process" according to the present disclosure.

«Example of Diagnostic Support Method Using Information Processing Device 10»

Figure 12:
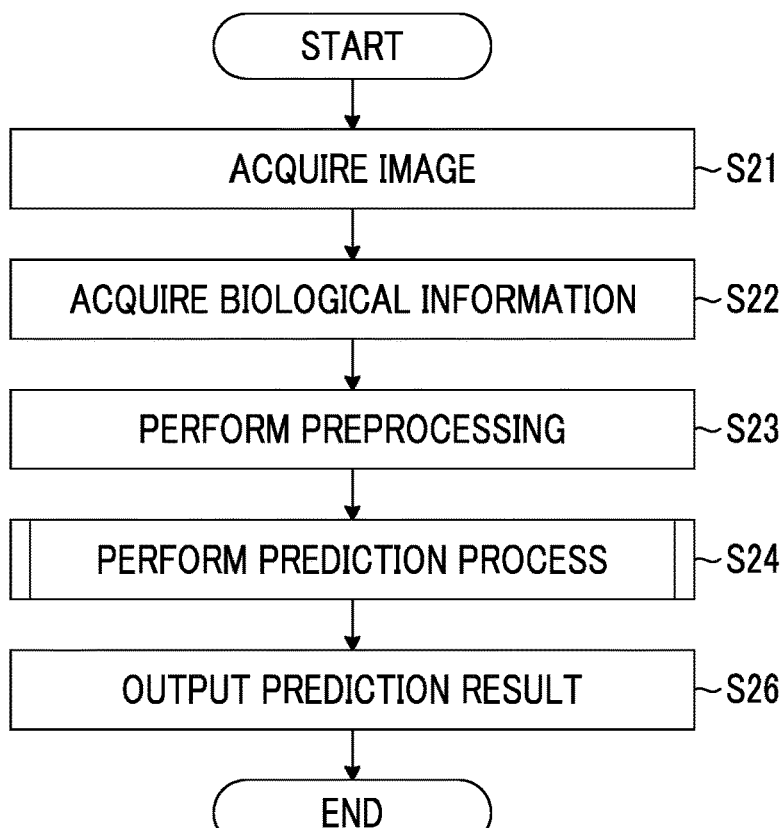
FIG. 12 is a flowchart illustrating a procedure of a diagnostic support method using the information processing device.

FIG. 12 is a flowchart illustrating an example of the procedure of the diagnostic support method using the information processing device 10. A learning data set is prepared as a preliminary preparation before the learning process is performed. That is, a plurality of learning data items which are combinations of the MRI images IM(p), the biological information BI(p), and the correct answer information CD(p) described with reference to FIG. 7 are prepared. The function of generating the learning data sets may be incorporated into the learning device 100 or may be incorporated into a device other than the learning device 100.

In Step S21, the information processing device 10 acquires an MRI image of the subject.

In Step S22, the information processing device 10 acquires the biological information of the subject. The order of the processes in Step S21 and Step S22 can be interchanged. Further, Step S21 and Step S22 may be performed at the same time or in parallel.

In Step S23, the preprocessing unit 222 of the information processing device 10 performs preprocessing on the input MRI image and biological information as necessary.

In Step S24, the information processing device 10 inputs the MRI image and the biological information to the prediction model 12 and performs the prediction process.

In Step S26, the information processing device 10 outputs the prediction result obtained by the prediction model 12. After Step S26, the information processing device 10 ends the flowchart illustrated in FIG. 12.

Figure 13:
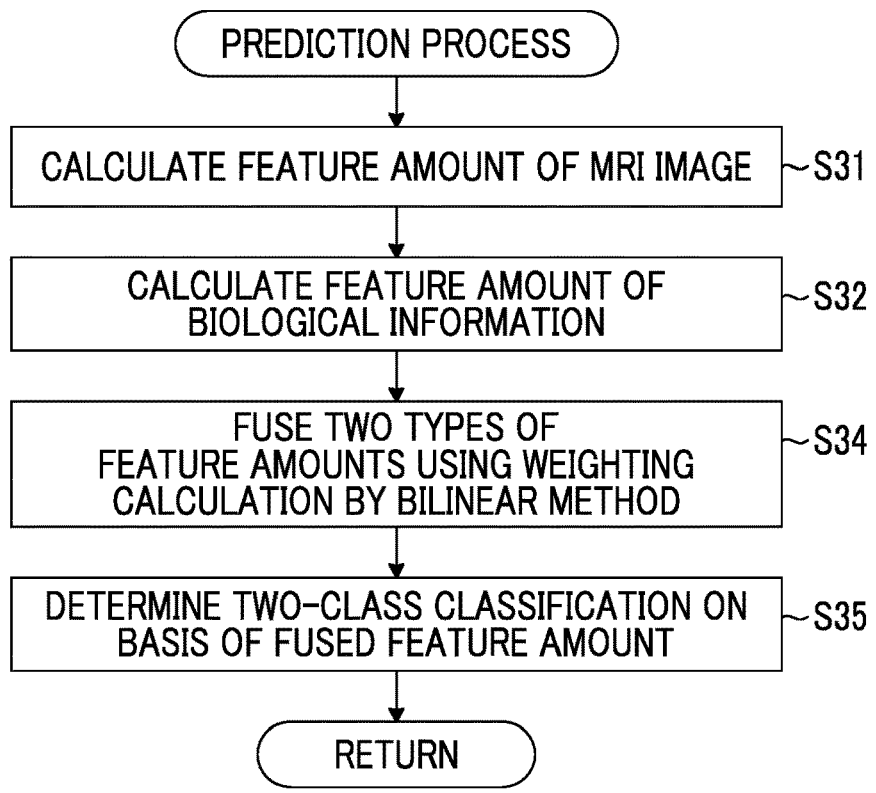
FIG. 13 is a flowchart illustrating an example of the content of a prediction process in Step S24 of FIG. 12.

FIG. 13 is a flowchart illustrating an example of the content of the prediction process (Step S24). The flowchart illustrated in FIG. 13 is applied to the process in Step S24 illustrated in FIG. 12. In Step S31 of FIG. 13, the prediction model 12 calculates the feature amount of the input MRI image. That is, the prediction model 12 calculates the first feature amount Fv1 from the MRI image according to a forward propagation path of the neural network 16.

In Step S32, the prediction model 12 calculates the feature amount of the input biological information. That is, the prediction model 12 connects elements of the biological information with the fully connected layer FC2 to calculate the second feature amount Fv2. The order of the processes in Step S31 and Step S32 can be interchanged. Further, Step S31 and Step S32 may be performed at the same time or in parallel.

In Step S34, the prediction model 12 fuses the two types of feature amounts obtained from Steps S31 and S32 using weighting calculation by the bilinear method to generate the third feature amount Fv3.

In Step S35, the prediction model 12 determines two-class classification on the basis of the third feature amount Fv3 which is the feature amount fused in Step S34.

After Step S35, the information processing device 10 ends the flowchart illustrated in FIG. 13 and returns to the flowchart illustrated in FIG. 12.

«Example of Hardware Configuration of Computer»

Figure 14:
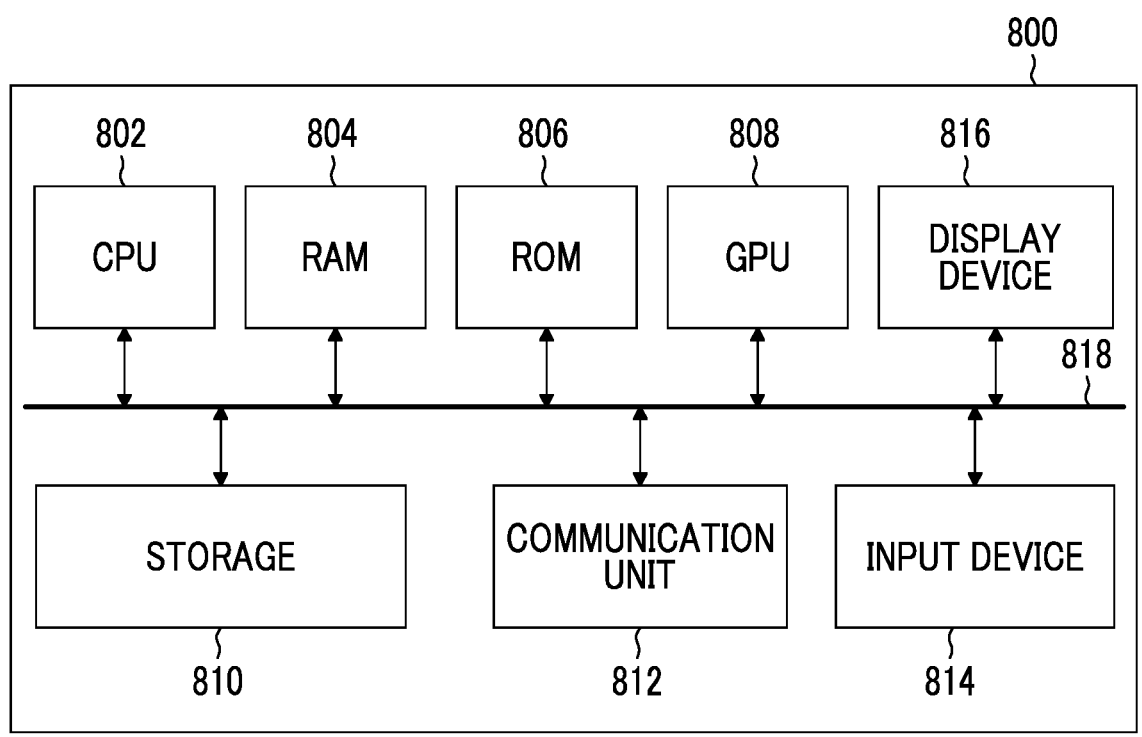
FIG. 14 is a block diagram illustrating an example of a hardware configuration of a computer.

FIG. 14 is a block diagram illustrating an example of the hardware configuration of a computer. A computer 800 may be a personal computer, a workstation, or a server computer. The computer 800 can be used as a device that has some or all of the information processing device 10, the image storage server 44, the in-hospital terminal device 50, the learning device 100, and the learning data storage unit 170 which have been described above or a plurality of functions thereof.

The computer 800 includes a central processing unit (CPU) 802, a random access memory (RAM) 804, a read only memory (ROM) 806, a graphics processing unit (GPU) 808, a storage 810, a communication unit 812, an input device 814, and a display device 816, and a bus 818. The graphics processing unit (GPU) 808 may be provided as needed.

The CPU 802 reads out various programs stored in, for example, the ROM 806 or the storage 810 and performs various processes. The RAM 804 is used as a work area of the CPU 802. Further, the RAM 804 is used as a storage unit that temporarily stores the read-out program and various types of data.

The storage 810 is configured to include, for example, a hard disk device, an optical disk, a magneto-optical disk, a semiconductor memory, or a storage device configured using an appropriate combination thereof. The storage 810 stores various programs, data, and the like necessary for, for example, the prediction process and/or the learning process. The program stored in the storage 810 is loaded to the RAM 804, and the CPU 802 executes the program such that the computer 800 functions as a unit for performing various processes prescribed by the program.

The communication unit 812 is an interface that performs a wired or wireless communication process with an external device to exchange information with the external device. The communication unit 812 can play the role of an information acquisition unit that receives the input of, for example, images.

The input device 814 is an input interface that receives various operations input to the computer 800. The input device 814 may be, for example, a keyboard, a mouse, a touch panel, other pointing devices, a voice input device, or an appropriate combination thereof.

The display device 816 is an output interface that displays various types of information. The display device 816 may be, for example, a liquid crystal display, an organic electroluminescence (OEL) display, a projector, or an appropriate combination thereof.

«For Program for Operating Computer»

A program that causes a computer to implement a portion or all of the processing function which is at least one of the prediction function or the learning function described in the above-described embodiment can be recorded on an optical disk, a magnetic disk, or a computer-readable medium, such as a semiconductor memory or other tangible non-transitory information storage media. Then, the program can be provided through the information storage medium.

Further, instead of the aspect in which the program is stored in the tangible non-transitory computer-readable medium and then provided, program signals may be provided as a download service using a telecommunication line such as the Internet.

In addition, a portion or all of the processing function which is at least one of the prediction function or the learning function described in the above-described embodiments may be provided as an application server, and a service that provides the processing function through a telecommunication line may be performed.

«For Hardware Configuration of Each Processing Unit»

For example, the following various processors are used as the hardware structure of processing units performing various processes such as the prediction model 12 illustrated in FIG. 1 and the like, the learning model 14 illustrated in FIG. 2 and the like, the information acquisition unit 121, the preprocessing unit 122, the error calculation unit 124, the optimizer 125, and the display control unit 130 illustrated in FIG. 6, the image acquisition unit 141, the biological information acquisition unit 142, the correct answer information acquisition unit 143, the parameter update amount calculation unit 151, the parameter update processing unit 152 illustrated in FIG. 8, the information acquisition unit 221, the preprocessing unit 222, the display control unit 230 illustrated in FIG. 10, and the image acquisition unit 241 and the biological information acquisition unit 242 illustrated in FIG. 11.

The various processors include, for example, a CPU which is a general-purpose processor executing a program to function as various processing units, a GPU which is a processor specializing in image processing, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types. For example, one processing unit may be configured by a plurality of FPGAs, a combination of a CPU and an FPGA, or a combination of a CPU and a GPU. Further, a plurality of processing units may be configured by one processor. A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As described above, various processing units are configured using one or more of the various processors as a hardware structure.

In addition, specifically, the hardware structure of the various processors is an electric circuit (circuitry) obtained by combining circuit elements such as semiconductor elements.

EXAMPLES

In the information processing device 10 according to the embodiment of the invention, it was determined whether or not a patient changed from MCI to Alzheimer's disease one year later using the MRI image, genotype, cognitive ability score, age, and gender of the patient, and the accuracy of the determination was 85% or more. The "determination" is included in the concept of "prediction". The accuracy of the determination is synonymous with the "accuracy of prediction".

In contrast, in the study described in Garam Lee, Kwangsik Nho, et al. "Predicting Alzheimer's disease progression using multi-modal deep learning approach", Scientific Reports 9, Article number: 1952 (2019), the same determination is performed using the MRI image, cerebrospinal fluid data, cognitive ability score, age, and gender of the patent. In this case, the accuracy of the determination is 76%.

The method according to the embodiment of the invention has a higher accuracy of determination than that in the method described in Garam Lee, Kwangsik Nho, et al. "Predicting Alzheimer's disease progression using multi-modal deep learning approach", Scientific Reports 9, Article number: 1952 (2019).

《Advantages of This Embodiment》

According to the information processing device 10 of the embodiment of the invention, it is possible to predict the future state of the patient with high accuracy using the MRI image and biological information of the patient.

《Assumed Execution Aspects》

As an aspect of using the dementia progression prediction function of the information processing device 10 according to this embodiment, for example, an aspect is considered in which a subject who is expected not to progress to Alzheimer's disease is excluded from a clinical trial in order to improve the accuracy of the clinical trial in the development of new drugs.

In other words, for the patient from which the prediction result indicating that "the patient does not progress to Alzheimer's disease" has been obtained by the prediction of the progression of dementia by the information processing device 10, it is difficult to determine whether or not the drug is effective even in a case in which the drug is administered. Therefore, it is considered to exclude the patient from the clinical trial.

In addition, as another usage aspect, the following aspect is considered: after a drug that suppresses the progression of Alzheimer's disease is sold, a patient who has a reaction to the drug, that is, a patient who is expected to develop Alzheimer's disease is identified in order to administer the drug only to the patient who has a reaction to the drug.

Modification Example 1

In the above-described embodiment, an example in which the state "after one year" is predicted has been described. However, the period condition of "after one year" is not limited to this example. The method for giving the correct answer information used for learning may be changed according to the purpose of the prediction to achieve the prediction for various periods such as "after 6 months", "after 18 months", or "after 2 years".

Modification Example 2

In the above-described embodiment, an example in which the progression of dementia of the MCI patient as the subject is predicted has been described. However, a healthy person may be included as the subject and may be classified into a class "no change" in the determination of class classification. Alternatively, a "healthy person" class may be provided among the class classification candidates. Data related to the healthy person is used as the learning data in order to achieve prediction related to the healthy person.

Modification Example 3

In the above-described embodiment, the network for two-class classification has been described as an example. However, the application scope of the technology of the present disclosure is not limited to this example. For example, a network for multi-class classification, such as three-or-more-class classification, may be applied. In addition, the technology of the present disclosure can be applied not only to the prediction model for class classification but also to a prediction model for solving a regression problem.

Modification Example 4

In the above-described embodiment, an example in which the MRI image is used has been described. However, the technology of the present disclosure is not limited to the MRI image, and images of other modalities may be used. For example, a CT image acquired by a CT apparatus may be used. In this case, a non-contrast CT image acquired by performing imaging without using a contrast medium or a contrast CT image acquired by performing imaging using a contrast medium may be used as the CT image. Further, a positron emission tomography (PET) image acquired by a PET apparatus, an optical coherence tomography (OCT) image acquired by an OCT apparatus, a three-dimensional ultrasonic image acquired by a three-dimensional ultrasonography apparatus, or the like may be used. Furthermore, the prediction technology according to the present disclosure can be applied not only to a three-dimensional tomographic image but also to various two-dimensional images. For example, the image to be processed may be a two-dimensional X-ray image.

Other Application Examples

In addition, the prediction technology according to the present disclosure can be applied not only to medical images but also to various images such as normal camera images. For example, the technology according to the present disclosure can be applied to the prediction of a future deterioration state after a lapse of a specific period from the image of a building such as a bridge. Non-image information used in combination with the image of the building, such as a bridge, may be, for example, at least one of a material forming the building, positional information indicating an installation site, a structural style, or inspection data of a periodic inspection, preferably, a combination of two or more of these items.

«For Information Used for Input»

In the technology according to the present disclosure, non-image data used in combination with image data includes information that is not directly related to the content of the image in order to improve the accuracy of prediction. The biological information used as an input in combination with the MRI image of the brain in order to predict the progression of dementia is an example of the information that is not directly related to the content of the MRI image. That is, the biological information includes information related to a matter that does not appear in the MRI image. The biological information is an example of "information related to a matter that does not appear in an image indicated by image data" in the present disclosure.

In addition, image data of an MRI image or the like is information at a specific timing when an object is imaged. So to speak, one image data item is "information at a point of time". On the other hand, the task of predicting future matters is the temporal question of how the matters will change from the present or the past to the future. Therefore, it is preferable to use non-image information having a "time" dimension, which is not included in the image data, in combination with the image data in order to improve the accuracy of prediction. For example, the genetic information exemplified by the genotype does not include information at a certain point of time, but includes information on how the patient changes from the past to the future or the possibility that the patient will change from the past to the future. As described above, information including information at a plurality of points of time can be construed as information having the time dimension. The genetic data is an example of "data of information including information at a plurality of points of time" in the present disclosure.

«For Past Prediction»

The technology of the present disclosure can also be applied to a process of predicting the aspect at a time in the past before the time when the image was captured. In this case, data indicating a known aspect before the time of imaging is used as correct answer information corresponding to the image data and the non-image data in the learning data.

An algorithm for predicting the past aspect before a specific period from the time of imaging is the same as the algorithm for predicting the aspect after the lapse of a specific period from the time of imaging.

«For Distillation Model and Derived Model»

It is possible to generate a derived model and/or a distillation model on the basis of the trained model generated by performing the learning method according to the present disclosure. The derived model is a derived trained model obtained by performing additional training on the trained model and is also referred to as a "reuse model". Here, the "additional training" means a process of further training the existing trained model using a different learning data set to generate new trained parameters. For example, the additional training is performed to maintain or improve the accuracy of the trained model or to adapt the trained model to a region different from the region originally trained.

On the other hand, the "distillation" means a process of performing machine learning, using the input to the existing trained model and the output result for the input as a learning data set for a new model, to generate a new trained model and/or trained parameters. The "distillation model" is an inference program (prediction model) into which trained parameters newly generated by distillation have been incorporated. The distillation model may have a network structure different from the original trained model.

It is possible to generate a derived model and/or a distillation model on the basis of the trained model obtained by performing the learning method according to the present disclosure. Therefore, it is understood that a method for generating the derived model and/or the distillation model, and the obtained derived model and/or distillation model belong to the technical scope of the present disclosure.

«Others»

The configurations described in the above-described embodiment and the items described in the modification examples can be appropriately combined and used, and some of the items can be replaced. It goes without saying that the invention is not limited to the above-described embodiment, and various modifications can be made without departing from the spirit of the invention.

«Additional Notes»

A summary of a specific example of a multi-modal deep learning technique for predicting the progression of Alzheimer's disease using a fusion process by a bilinear method, which is described in English, is disclosed below.

AD (Alzheimer's Disease) which causes declination of cognitive function is one of the most severe social issues in the world. It has already been known that AD cannot be cured and treatment can only delay its progression. Therefore, it is very important to detect AD In this research, we developed a novel multi-modal deep learning method to predict conversion from MCI (Mild Cognitive Impairment), which is the stage between cognitively normal older people and AD. In our method, the multi-modal input data are defined as MRI images and clinical data including several cognitive scores, APoEgenotype, gender and age obtained from ADNI (Alzheimer's Disease Neuroimaging Initiative cohort). Our criteria of selecting these input data are that they are mostly obtained by non-invasive examination. The proposed method integrates features obtained from MRI images and clinical data effectively by using bi-linear fusion. Bi-linear fusion computes the products of all elements between image and clinical features, where the correlation between them are included. That led a big improvement of prediction accuracy in the experiment. The prediction model using bi-linear fusion achieved to predict conversion in one year with 84.8% accuracy, comparing with 75.3% accuracy using linear fusion. The proposed method is useful for screening examination for AD or deciding a stratification approach within clinical trials since it achieved a high accuracy while the input data is relatively easy to be obtained.

EXPLANATION OF REFERENCES

10: information processing device
12: prediction model
14: learning model
16: neural network
40: medical image information system
42: three-dimensional imaging apparatus
44: image storage server
46: communication line
50: in-hospital terminal device
60: router
66: wide area communication network
100: learning device
102: processor
104: computer-readable medium
106: input/output Interface
108: communication Interface
110: bus
114: input device
116: display device
121: information acquisition unit
122: preprocessing unit
124: error calculation unit
125: optimizer
130: display control unit
141: image acquisition unit
142: biological information acquisition unit
143: correct answer information acquisition unit
151: parameter update amount calculation unit
152: parameter update processing unit
170: learning data storage unit
202: processor
204: computer-readable medium
206: input/output interface
208: communication Interface
210: bus
214: input device
216: display device
221: information acquisition unit
222: preprocessing unit
230: display control unit
241: image acquisition unit
242: biological information acquisition unit
800: computer
802: CPU
804: RAM
806: ROM
808: GPU
810: storage
812: communication unit
814: input device
816: display device
818: bus
IM: MRI image
BI: biological information
CD: correct answer information
LD: learning data
FC1: fully connected layer
FC2: fully connected layer
FC3: fully connected layer
FU: fusion layer
Fv1: first feature amount
Fv2: second feature amount
Fv3: third feature amount
S1 to S6: step of learning method
S21 to S26: step of diagnostic support method
S31 to S35: step of prediction process

What is claimed is:

1. An information processing device comprising:
   an information acquisition unit that receives an input of image data and non-image data related to a target matter; and
   a prediction unit that predicts an aspect related to the matter at a time different from a time when the image data is captured on the basis of the image data and the non-image data input through the information acquisition unit,
   wherein the prediction unit performs weighting calculation by a calculation method, which outputs a combination of products of elements of a first feature amount calculated from the image data and a second feature amount calculated from the non-image data, to calculate a third feature amount in which the first feature amount and the second feature amount are fused and performs the prediction on the basis of the third feature amount, and
   wherein the non-image data includes data of information related to a matter that does not appear in an image indicated by the image data.

2. The information processing device according to claim 1,
   wherein the prediction unit includes a trained prediction model that has been subjected to machine learning so as to receive the input of the image data and the non-image data and to output, as a result of the prediction, information indicating the aspect related to the matter at a time different from the time when the image data is captured.

3. The information processing device according to claim 1,
   wherein the prediction unit is configured using a neural network.

4. The information processing device according to claim 1,
   wherein the prediction unit performs a class classification process of determining which of a plurality of classes corresponding to each of a plurality of candidates for the aspect related to the matter at a time different from the time when the image data is captured the aspect belongs to in response to the input of the image data and the non-image data and outputs a result of the class classification process.

5. The information processing device according to claim 1,
   wherein the prediction unit performs a two-class classification process of determining whether an aspect after a lapse of a specific period from the time when the image data is captured or a past aspect before a specific period from the time when the image data is captured as the aspect related to the matter at a time different from the time when the image data is captured is a first state or a second state different from the first state and outputs a result of the two-class classification process.

6. The information processing device according to claim 1,
wherein the prediction unit includes:
a first processing unit that calculates the first feature amount from the image data;
a second processing unit that calculates the second feature amount from the non-image data; and
a third processing unit that performs the weighting calculation by the calculation method that outputs the combination of the products of the elements using the first feature amount and the second feature amount to calculate the third feature amount.

7. The information processing device according to claim 6,
wherein the weighting calculation performed by the third processing unit includes a process of multiplying the first feature amount and the second feature amount at a random ratio.

8. The information processing device according to claim 6,
wherein the first processing unit is configured using a first neural network including a plurality of convolutional layers and a first fully connected layer, and
the second processing unit is configured using a second neural network including a second fully connected layer.

9. The information processing device according to claim 8, further comprising:
a third fully connected layer that calculates a final output value from the third feature amount.

10. The information processing device according to claim 1,
wherein the non-image data includes data of information including information at a plurality of points of time.

11. The information processing device according to claim 1,
wherein the target matter is a health condition of a subject,
the image data is a medical image obtained by imaging the subject,
the non-image data includes biological information of the subject, and
the prediction unit predicts the health condition of the subject after a lapse of a specific period from a time when the medical image is captured or the health condition of the subject at a past time before a specific period from the time when the medical image is captured.

12. The information processing device according to claim 1,
wherein the target matter is a disease state of a subject with mild cognitive impairment,
the image data is a magnetic resonance Imaging (MRI) image obtained by imaging a brain of the subject,
the non-image data includes at least one of blood test data, genetic data, or a cognitive ability score of the subject, and age and gender of the subject, and
the prediction unit predicts whether the disease state of the subject will be Alzheimer's disease or the mild cognitive impairment after a lapse of a specific period from a time when the MRI image is captured.

13. The information processing device according to claim 12,
wherein the prediction unit excludes the subject, from which a prediction result indicating that the disease state of the subject will be the mild cognitive impairment after the lapse of the specific period, from subjects of a clinical trial.

14. An information processing device comprising:
a processor; and
a non-transitory computer-readable medium on which a program executed by the processor is recorded,
wherein, according to commands of the program, the processor receives an input of image data and non-image data related to a target matter, performs weighting calculation by a calculation method, which outputs a combination of products of elements of a first feature amount calculated from the image data and a second feature amount calculated from the non-image data, to calculate a third feature amount in which the first feature amount and the second feature amount are fused, and predicts an aspect related to the matter at a time different from a time when the image data is captured on the basis of the third feature amount, and
wherein the non-image data includes data of information related to a matter that does not appear in an image indicated by the image data.

15. A non-transitory computer-readable recording medium that stores commands for causing, when read by a computer, the computer to implement the functions comprising:
a function of receiving an input of image data and non-image data related to a target matter;
a function of performing weighting calculation by a calculation method, which outputs a combination of products of elements of a first feature amount calculated from the image data and a second feature amount calculated from the non-image data, to calculate a third feature amount in which the first feature amount and the second feature amount are fused; and
a function of predicting an aspect related to the matter at a time different from a time when the image data is captured on the basis of the third feature amount, and
wherein the non-image data includes data of information related to a matter that does not appear in an image indicated by the image data.

16. A non-transitory trained model that has been subjected to machine learning so as to receive an input of image data and non-image data related to a target matter and to output information predicted from the image data and the non-image data, the non-transitory trained model causing a computer to execute:
performing weighting calculation by a calculation method, which outputs a combination of products of elements of a first feature amount calculated from the image data and a second feature amount calculated from the non-image data, to calculate a third feature amount in which the first feature amount and the second feature amount are fused; and
outputting the information indicating the aspect related to the matter at a time different from a time when the imaging data is captured on the basis of the third feature amount, and wherein the non-image data includes data of information related to a matter that does not appear in an image indicated by the image data.

17. The non-transitory trained model according to claim 16,
wherein the target matter is a health condition of a subject,
the image data is a medical image obtained by imaging the subject,
the non-image data includes biological information of the subject, and
the non-transitory trained model predicts the health condition of the subject after a lapse of a specific period from a time when the medical image is captured or the health condition of the subject at a past time before a specific period from the time when the medical image is captured.

18. A diagnostic support device comprising:
a non-transitory computer-readable medium on which the non-transitory trained model according to claim 16 is recorded; and
a processor that operates according to the non-transitory trained model.

19. A learning device comprising:
a processor; and
a non-transitory computer-readable medium on which a learning program executed by the processor is recorded,
wherein, according to commands of the learning program, the processor acquires learning data including image data and non-image data related to a target matter and data indicating a known aspect of the matter corresponding to a combination of the image data and the non-image data, inputs the image data and the non-image data to the learning model, and performs machine learning on the learning model using the image data and the non-image data such that prediction information indicating an aspect related to the matter at a time different from a time when the image data is captured is output, and
the learning model performs weighting calculation by a calculation method, which outputs a combination of products of elements of a first feature amount calculated from the image data and a second feature amount calculated from the non-image data, to calculate a third feature amount in which the first feature amount and the second feature amount are fused and outputs the prediction information on the basis of the third feature amount, and wherein the non-image data includes data of information related to a matter that does not appear in an image indicated by the image data.

20. A prediction model generation method comprising:
acquiring learning data including image data and non-image data related to a target matter and data indicating a known aspect of the matter corresponding to a combination of the image data and the non-image data; and
performing machine learning on the learning model using the learning data to generate a trained prediction model that outputs prediction information indicating an aspect related to the matter at a time different from a time when the image data is captured in response to an input of the image data and the non-image data,
wherein the learning model performs weighting calculation by a calculation method, which outputs a combination of products of elements of a first feature amount calculated from the image data and a second feature amount calculated from the non-image data, to calculate a third feature amount in which the first feature amount and the second feature amount are fused and outputs the prediction information on the basis of the third feature amount, and wherein the non-image data includes data of information related to a matter that does not appear in an image indicated by the image data.

* * * * *